United States Patent
Dagvadorj et al.

(10) Patent No.: US 12,168,037 B2
(45) Date of Patent: Dec. 17, 2024

(54) INTRACELLULAR IL-1 ALPHA PEPTIDE METHODS AND COMPOSITIONS

(71) Applicant: CEDARS-SINAI MEDICAL CENTER, Los Angeles, CA (US)

(72) Inventors: Jargalsaikhan Dagvadorj, Los Angeles, CA (US); Moshe Arditi, Encino, CA (US); Gantsetseg Tumurkhuu, Los Angeles, CA (US); Janet Markman, Encino, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1051 days.

(21) Appl. No.: 16/963,421

(22) PCT Filed: Jan. 23, 2019

(86) PCT No.: PCT/US2019/014732
§ 371 (c)(1),
(2) Date: Jul. 20, 2020

(87) PCT Pub. No.: WO2019/147658
PCT Pub. Date: Aug. 1, 2019

(65) Prior Publication Data
US 2021/0060131 A1 Mar. 4, 2021

Related U.S. Application Data

(60) Provisional application No. 62/621,461, filed on Jan. 24, 2018.

(51) Int. Cl.
| | | |
|---|---|---|
| *A61K 38/20* | (2006.01) | |
| *A61K 38/08* | (2019.01) | |
| *A61P 35/00* | (2006.01) | |
| *A61P 35/04* | (2006.01) | |
| *C07K 14/545* | (2006.01) | |

(52) U.S. Cl.
CPC .......... *A61K 38/2006* (2013.01); *A61P 35/00* (2018.01); *A61P 35/04* (2018.01); *C07K 14/545* (2013.01); *A61K 38/08* (2013.01)

(58) Field of Classification Search
CPC .. A61K 38/2006; A61K 38/08; C07K 14/545; A61P 35/04; A61P 35/00
See application file for complete search history.

(56) References Cited

U.S. PATENT DOCUMENTS

| | | |
|---|---|---|
| 7,176,179 B1 | 2/2007 | Pollock et al. |
| 2006/0094663 A1 | 5/2006 | Chemtob et al. |
| 2015/0023870 A1 | 1/2015 | Chang et al. |

FOREIGN PATENT DOCUMENTS

| | | |
|---|---|---|
| EP | 0551200 A1 | 7/1993 |
| EP | 2764009 A1 | 8/2014 |
| WO | 20190147658 A1 | 8/2019 |

OTHER PUBLICATIONS

International Search Report and Written Opinion for PCT/US2019/014732, dated Apr. 9, 2019, 9 pages.
Elstrom et al., Akt Stimulates Aerobic Glycolysis in Cancer Cells, Cancer Research, 2004, vol. 64(11), pp. 3892-3899.
Style et al., Signaling through interleukin-1 type 1 receptor diminishes Haemophilus somnus lipooligosaccharide-mediated apoptosis of endothelial cells, Microbial Pathogenesis, 2005, vol. 39(4), pp. 121-130.
Apte et al., The involvement of IL-1 in tumorigenesis, tumor invasiveness, metastasis and tumor-host interactions, Cancer Metastasis Rev., 2006, vol. 25, pp. 387-408.

*Primary Examiner* — Li N Komatsu
(74) *Attorney, Agent, or Firm* — Linda B. Huber; Nixon Peabody LLP

(57) ABSTRACT

Described herein are methods and compositions for the treatment of cancer and cancer metastasis. Methods for the reduction or prevention of cancer metastasis are also described. In particular, the present invention discloses the use of the IL-1α pro-piece peptide in the treatment cancer and cancer metastasis.

7 Claims, 14 Drawing Sheets
Specification includes a Sequence Listing.

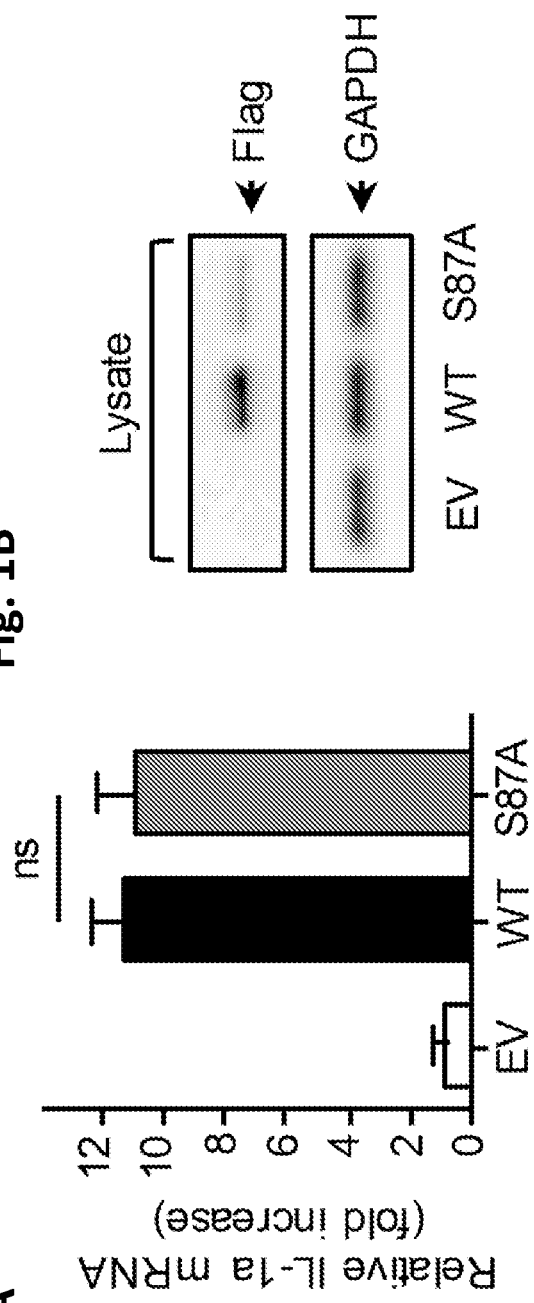
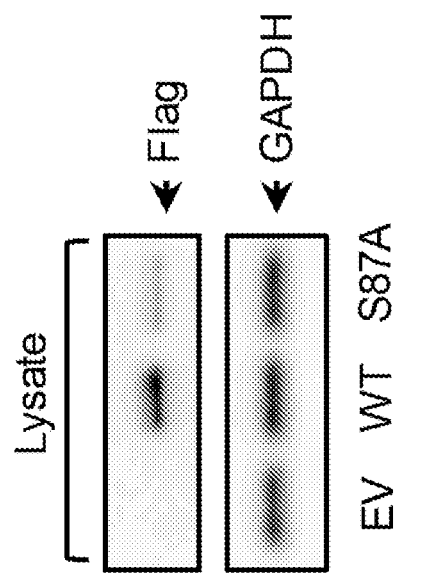
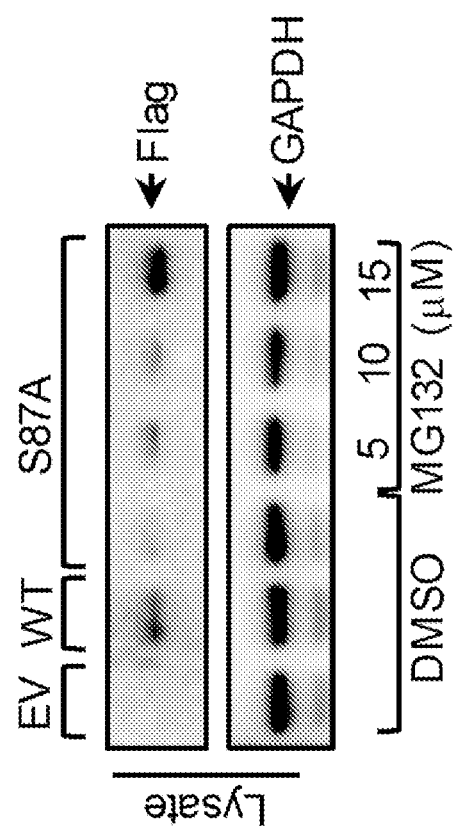
Fig. 1A
Fig. 1B
Fig. 1C

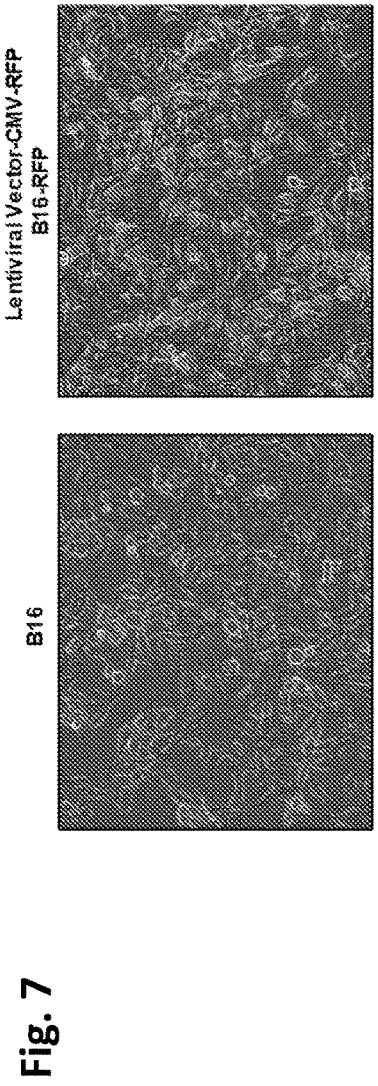
Fig. 7
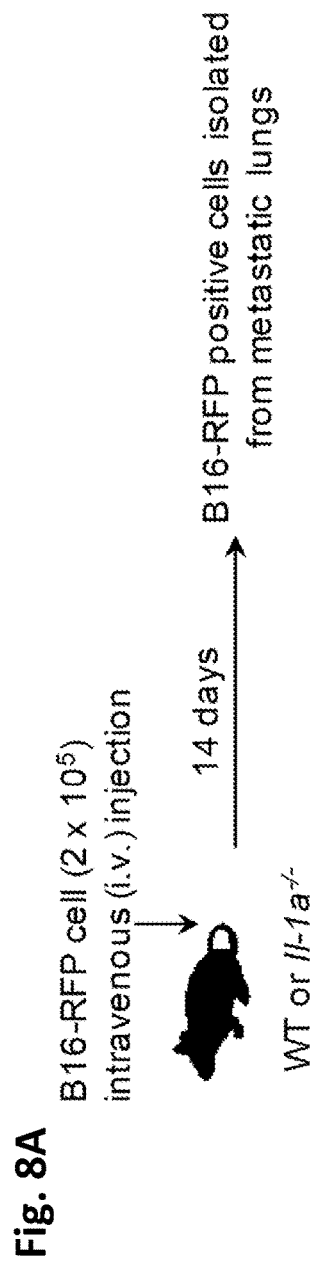
Fig. 8A
Fig. 8B
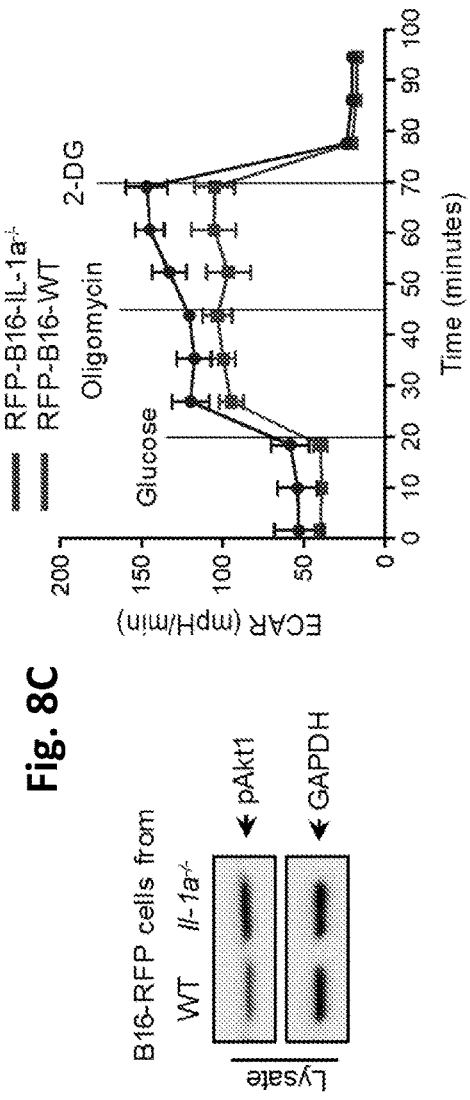
Fig. 8C

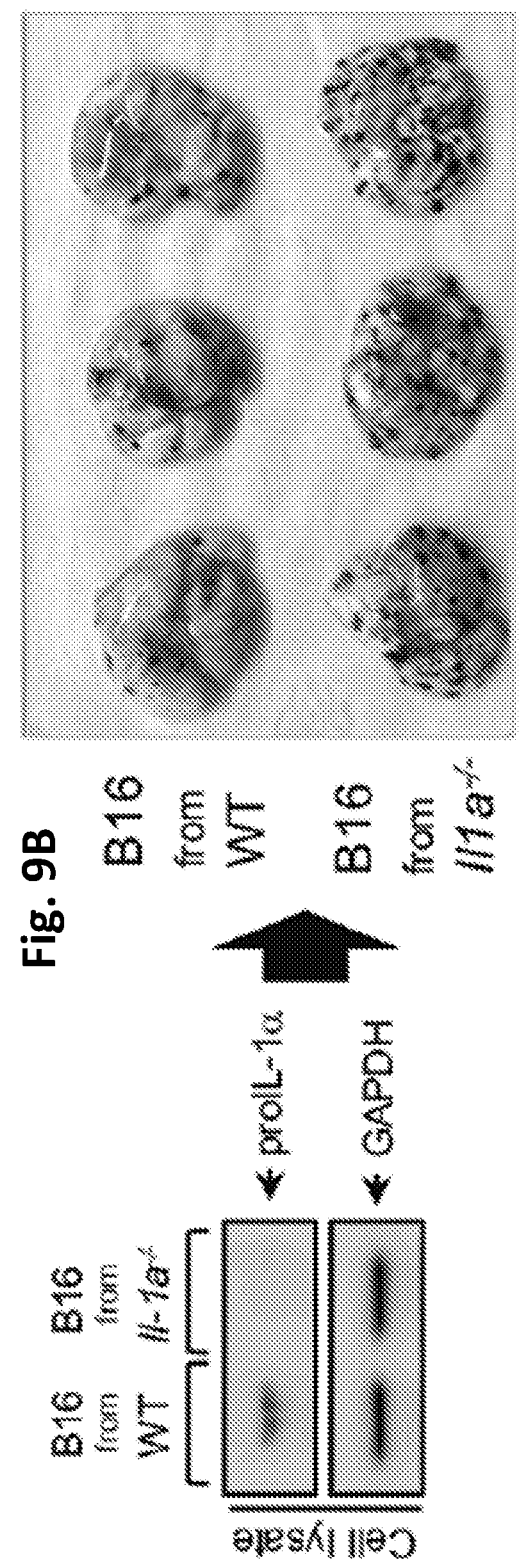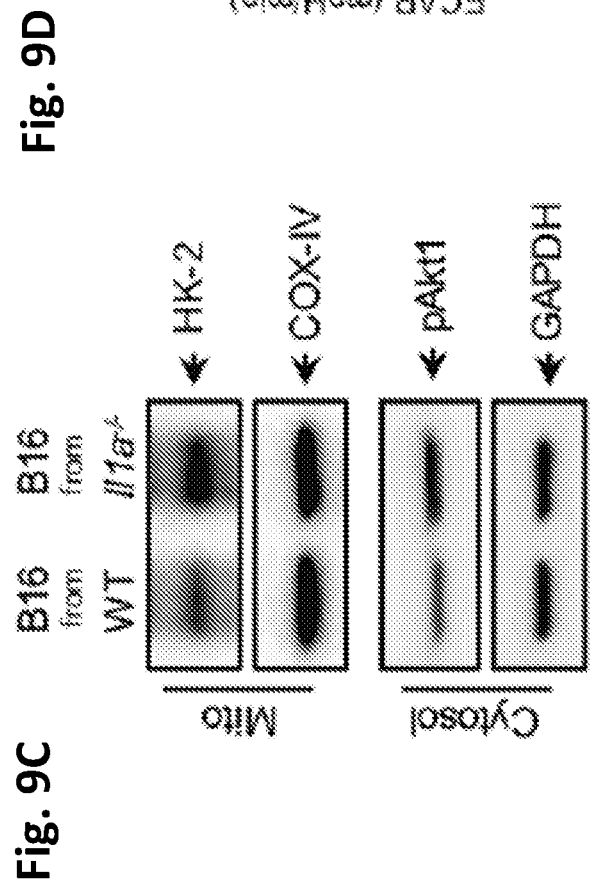
Fig. 9A
Fig. 9B
Fig. 9C
Fig. 9D

Akt1 substrate consensus motif

Human IL-1α: N-VATNGKVLKKRRLSLS-C
Mouse IL-1a: N-ATSSNGKILKKRRLSFS-C

SPDIA peptide (SEQ ID NO:1)
-GKVLKKRRLSL-

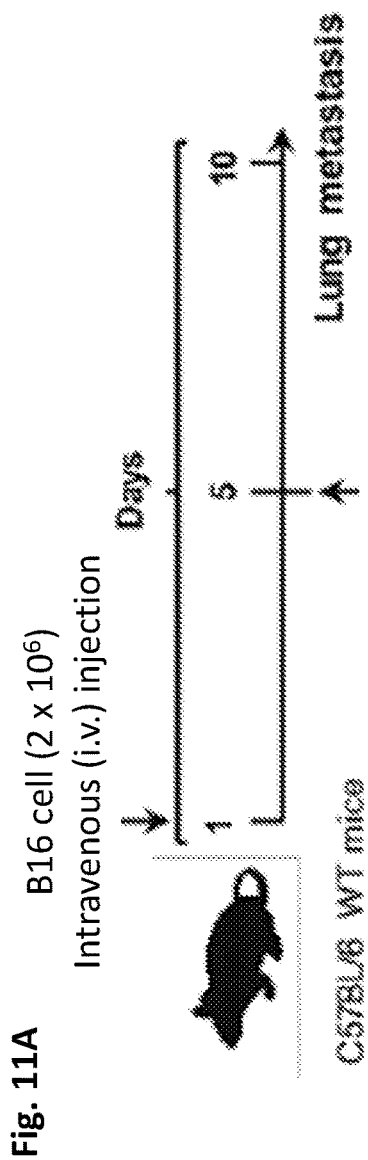
Fig. 11A
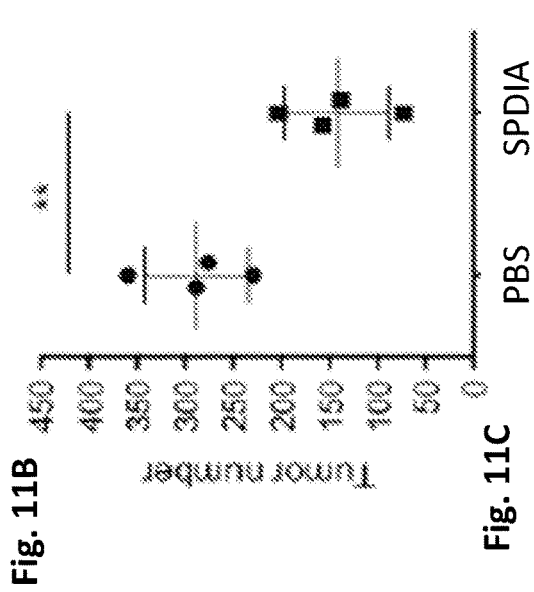
Fig. 11B
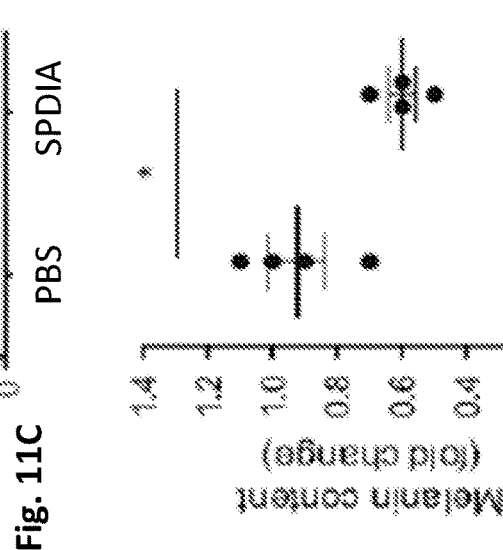
Fig. 11C
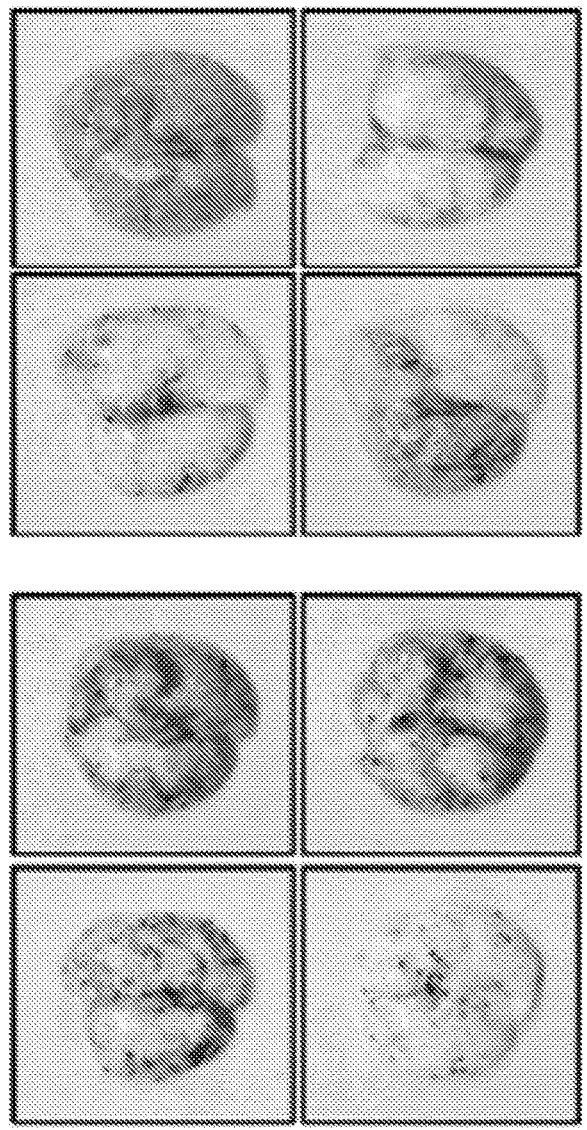

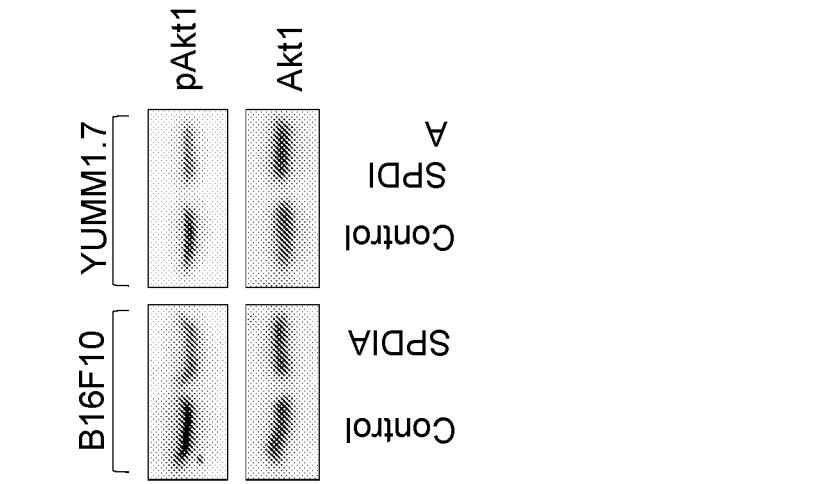
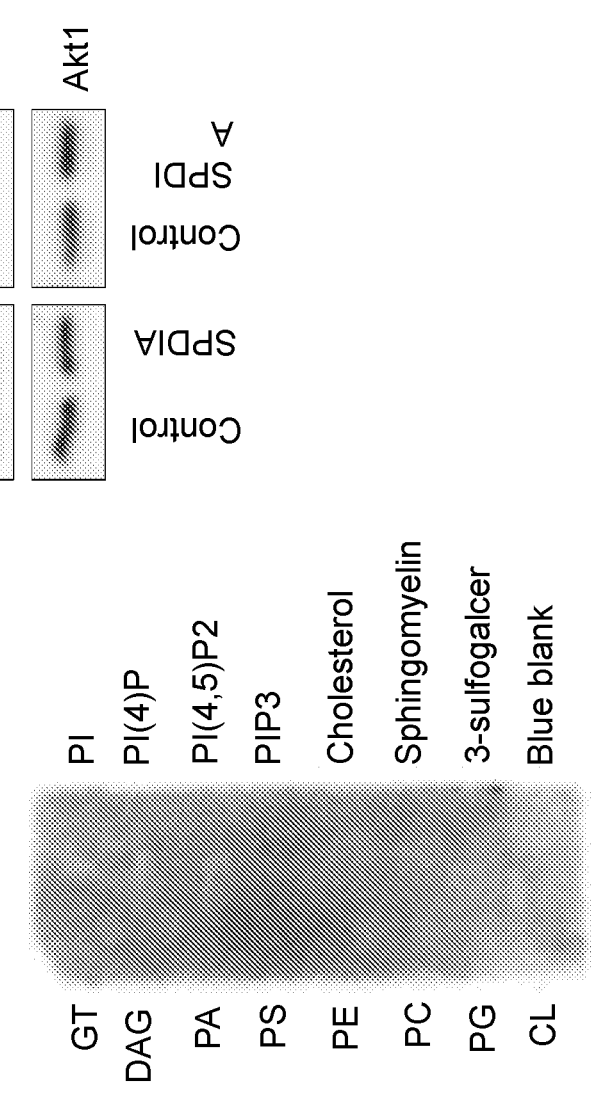
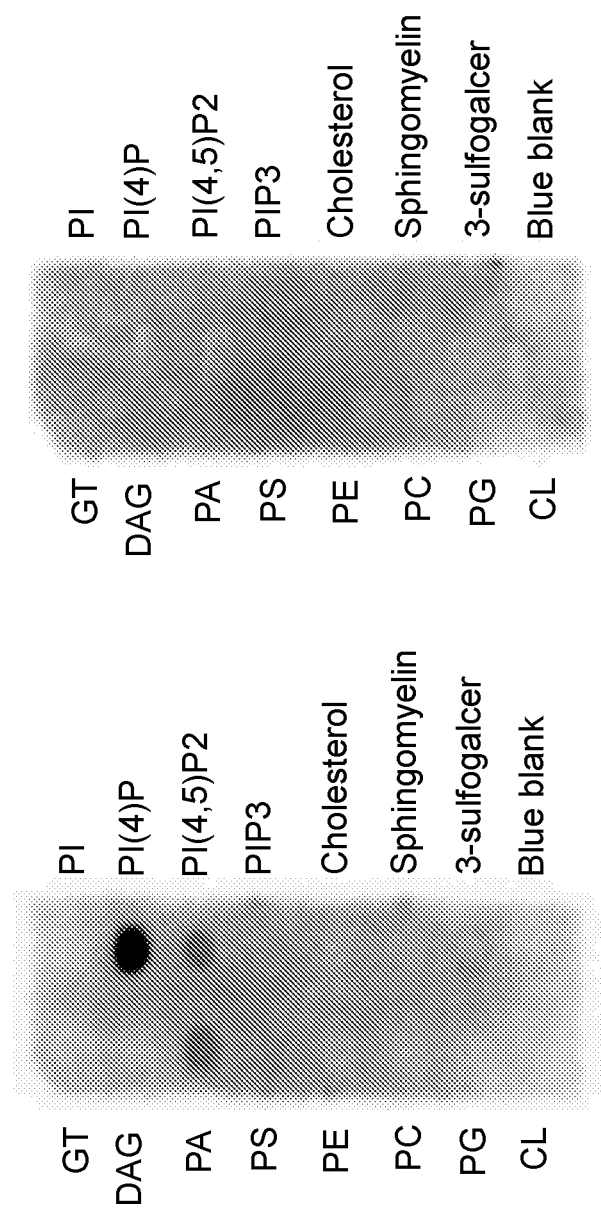

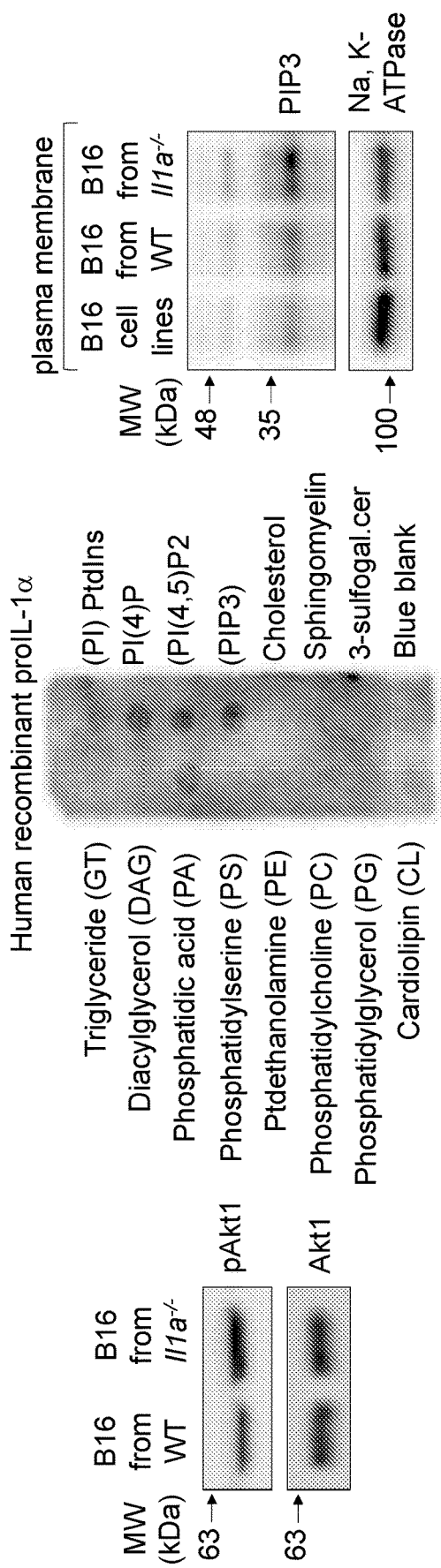

```
                        SEQUENCE LISTING

<160> NUMBER OF SEQ ID NOS: 9

<210> SEQ ID NO 1
<211> LENGTH: 11
<212> TYPE: PRT
<213> ORGANISM: Homo sapiens

<400> SEQUENCE: 1

Gly Lys Val Leu Lys Lys Arg Arg Leu Ser Leu
1               5                   10

<210> SEQ ID NO 2
<211> LENGTH: 18
<212> TYPE: PRT
<213> ORGANISM: Homo sapiens

<400> SEQUENCE: 2

Thr Ser Ser Asn Gly Lys Ile Leu Lys Lys Arg Arg Leu Ser Phe Ser
1               5                   10                  15

Glu Thr

<210> SEQ ID NO 3
<211> LENGTH: 19
<212> TYPE: PRT
<213> ORGANISM: Artificial Sequence
<220> FEATURE:
<223> OTHER INFORMATION: synthetic construct

<400> SEQUENCE: 3

Tyr Gly Arg Lys Lys Arg Arg Gln Arg Arg Leu Lys Lys Arg Arg
1               5                   10                  15

Leu Ser Leu

<210> SEQ ID NO 4
<211> LENGTH: 17
<212> TYPE: PRT
<213> ORGANISM: Mouse

<400> SEQUENCE: 4

Ala Thr Ser Ser Asn Gly Lys Ile Leu Lys Lys Arg Arg Leu Ser Phe
1               5                   10                  15

Ser

<210> SEQ ID NO 5
<211> LENGTH: 6
<212> TYPE: PRT
<213> ORGANISM: Homo sapiens

<400> SEQUENCE: 5

Lys Lys Arg Arg Leu Ser
1               5

<210> SEQ ID NO 6
<211> LENGTH: 8
<212> TYPE: PRT
<213> ORGANISM: Homo sapiens

<400> SEQUENCE: 6

Leu Lys Lys Arg Arg Leu Ser Leu
```

```
<210> SEQ ID NO 7
<211> LENGTH: 11
<212> TYPE: PRT
<213> ORGANISM: Artificial Sequence
<220> FEATURE:
<223> OTHER INFORMATION: synthetic construct

<400> SEQUENCE: 7

Tyr Gly Arg Lys Lys Arg Arg Gln Arg Arg Arg
1               5                   10

<210> SEQ ID NO 8
<211> LENGTH: 19
<212> TYPE: PRT
<213> ORGANISM: Artificial Sequence
<220> FEATURE:
<223> OTHER INFORMATION: synthetic construct

<400> SEQUENCE: 8

Tyr Gly Arg Lys Lys Arg Arg Gln Arg Arg Arg Leu Ala Lys Ala Arg
1               5                   10                  15

Leu Ala Leu

<210> SEQ ID NO 9
<211> LENGTH: 11
<212> TYPE: PRT
<213> ORGANISM: Artificial Sequence
<220> FEATURE:
<223> OTHER INFORMATION: synthetic construct

<400> SEQUENCE: 9

Gly Lys Val Leu Lys Lys Ala Ala Leu Ser Leu
1               5                   10
```

INTRACELLULAR IL-1 ALPHA PEPTIDE METHODS AND COMPOSITIONS

CROSS-REFERENCE TO RELATED APPLICATIONS

This application is a National Phase of International Application No. PCT/US2019/014732 filed Jan. 23, 2019, which designated the U.S. and that International Application was published under PCT Article 21 (2) in English, which includes a claim of priority under 35 U.S.C. § 119 (e) to U.S. provisional patent application No. 62/621,461, filed Jan. 24, 2018, the entirety of which is hereby incorporated by reference.

STATEMENT REGARDING FEDERALLY-SPONSORED RESEARCH

This invention was made with government support under Grant Nos. AI072726 and AI126368 awarded by National Institutes of Health. The government has certain rights in the invention.

FIELD OF THE INVENTION

The invention relates to intracellular IL-1α peptide and methods and compositions for treating cancer and/or metastasis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Metastasis normally occurs in two major phases: physical translocation of cancer cells from the primary tumor to a distant tissue and then colonization within that organ. Once metastases have been established, current treatments are much less likely to be curative. However, metastatic colonization is an inefficient process in which most circulating cancer cells die and only a minority of those that survive form tumors. An improved understanding of the mechanistic determinants of such colonization is needed to better prevent and treat metastatic cancer. Elucidating the underlying cause of metastatic inefficiency of tumor cells, and the role of contributing factors that influence the survival and tumor-initiating activity of disseminate cells are important determinants of metastasis and are therapeutic targets for preventing metastasis.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method of treating, preventing, reducing the likelihood of having and/or ameliorating cancer in a subject in need thereof, comprising: administering a therapeutically effective dosage of a pro-IL-1α peptide, a pro-IL-1α peptide mimic or both to the subject. In various embodiments, the pro-IL-1α peptide mimic can be a IL-1α pro-piece peptide. In various embodiments, the pro-IL-1α peptide mimic can comprise SEQ ID NO: 1.

In various embodiments, the method can further comprise providing a composition comprising the pro-IL-1α peptide, a pro-IL-1α peptide mimic or both.

In various embodiments, the cancer can be melanoma and/or lung cancer.

In various embodiments, treating and/or ameliorating cancer in a subject can result in reduced tumor burden. In various embodiments, the reduced tumor burden can comprise a reduced tumor volume and/or tumor mass. In various embodiments, the administering a therapeutically effective dosage of the pro-IL-1α peptide, a pro-IL-1α peptide mimic or both can reduce Akt1 activation and glycolysis in the cancer cells. In various embodiments, the AKT1 phosphorylation can be reduced. In various embodiments, the glycolic rate can be decreased. In various embodiments, melanoma and/or lung cancer can be treated, prevented and/or ameliorated.

Various embodiments provide for a method for reducing, reducing the likelihood of, and/or preventing cancer metastasis in a subject in need thereof, comprising: administering a therapeutically effective dosage of a pro-IL-1α peptide, a pro-IL-1α peptide mimic or both to the subject. In various embodiments, the pro-IL-1α peptide mimic can be a IL-1α pro-piece peptide. In various embodiments, the pro-IL-1α peptide mimic can comprise SEQ ID NO: 1.

In various embodiments, the method can further comprise providing a composition comprising pro-IL-1α peptide, a pro-IL-1α peptide mimic or both. In various embodiments, lung and/or melanoma metastasis can be reduced.

In various embodiments, the administering a therapeutically effective dosage of the pro-IL-1α peptide, a pro-IL-1α peptide mimic or both can reduce Akt1 activation and glycolysis in the cancer cells. In various embodiments, the AKT1 phosphorylation can be reduced. In various embodiments, the glycolic rate can be decreased. In various embodiments, lung cancer and/or melanoma metastasis can be reduced or prevented.

Various embodiments provide for a pharmaceutical composition, comprising: a therapeutically effective amount of a pro-IL-1α peptide mimic; and a pharmaceutically acceptable carrier. In various embodiments, the pro-IL-1α peptide mimic can be a IL-1α pro-piece peptide. In various embodiments, the pro-IL-1α peptide mimic can comprise SEQ ID NO:1.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

FIGS. 1A-1C depict in accordance with various embodiments of the invention, that serine phosphorylation is required for IL-1α protein stability. FIG. 1A) Relative expression of IL-1α mRNA by qPCR. FIG. 1B) Western Blot of IL-1α protein level in cell lysates. FIG. 1C) Western blot of IL-1α in cell lysates of cells treated with DMSO or MG132 for 5 hours.

FIG. 4A) Experimental Schematic (top), metastatic lungs (bottom images). FIG. 4B) Quantification of tumor number in TAT-Control and TAT-IL-1α. FIG. 4C) Melanin content of the metastatic lungs in TAT-Control and TAT-IL-1α.

FIG. 5A) Female wild-type (WT) mice were injected with B16 melanoma cells (subcutaneously). The mimic peptide or PBS was injected intravenously on day 8 and 10 in the tail vein, and on day 15 tumor mice were sacrificed and tumors were analyzed. FIG. 5B) Representative images of tumor mice. FIG. 5C) Quantification of tumor volume (mm$^3$). FIG. 5D) Quantification of tumor mass (mg). n=5

FIG. 6A) Images of metastatic lungs. FIG. 6B) Quantification of tumor number. *p<0.001, n=7; p<0.01, n=7 FIG. 6C) Quantification of melanin content in the lungs. *p<0.001, n=7; p<0.01, n=7 FIG. 6D) Experimental scheme and representative tumor pictures. FIG. 6E) Quantification of tumor volume, *p<0.001, p<0.01, n=3.

FIG. 7 depicts in accordance with various embodiments of the invention, FRP stable expressing B16 cells. Lentiviral vector-CMV-RFP transfected into B16 cells and selected by Puromycin. RFP expression was measured by fluorescence microscopy.

FIGS. 8A-8C depict in accordance with various embodiments of the invention, differences of glycolytic rate in B16-RFP cells obtained from metastatic lungs of WT or IL-1α$^{-/-}$ mice. FIG. 8A) Experimental scheme. FIG. 8B) Western Blot of Akt1 activation in WT or IL-1α$^{-/-}$ cell lysates. GAPDH was used as a loading control. FIG. 8C) Extracellular acidification rate (ECAR) was measured by Seahorse and compared over time in WT or IL-1α$^{-/-}$ mice.

FIGS. 9A-9D depict in accordance with various embodiments of the invention, proIL-1α expression in B16 cells reduced melanoma metastasis. FIG. 9A) IL-1α protein level in cell lysates was determined by WB. FIG. 9B) Representative lung pictures from WT and IL-1α mice, n=3. FIG. 9C) HK-2 and pAkt1 was determined by WB. COX-IV and GAPDH was used as a loading control. FIG. 9D) Extracellular acidification rate (ECAR) was measured by Seahorse and compared over time in WT or IL-1α$^{-/-}$ mice.

FIG. 10A) Human N-terminal IL-1α pro-piece (LAPP) peptide (iIL-1α-peptide). FIG. 10B) HK-2 and pAkt1 in cytosolic and mitochondrial fraction were determined by WB. COX-IV and GAPDH was used as a loading controls. FIG. 10C) Extracellular acidification rate (ECAR) was measured by Seahorse and compared over time in PBS and iIL-1α-peptide treated mice.

FIGS. 11A-11C depict in accordance with various embodiments of the invention, that the iIL-1α-peptide reduces melanoma colonization in the lung. FIG. 11A) Experimental scheme and representative lung pictures. FIG. 11B) Quantification of tumor number, **p<0.01. FIG. 11C) Quantification of melanin content, *p<0.05. n=4.

FIGS. 12A-12F depict in accordance with various embodiments of the invention, that the iIL-1α-peptide reduces cutaneous melanoma tumor. FIG. 12A-12B) Membrane lipid strips were incubated with (5 μg) SPDIA or Control peptide and detected by ECL. FIG. 12C) B16 or YUMM1.7 cells were treated with SPDIA or Control peptide (40 μg/ml) for 5 h, and pAkt1 and Akt1 in cell lysate were determined by WB. FIG. 12D) Experimental scheme. FIG. 12E) tumor pictures. FIG. 12F) Quantification of tumor volume,  p<0.05. and Quantification of tumor mass,  p<0.05. n=5.

FIG. 13A) representative lung pictures, FIG. 13B) tumor numbers per lung, (n=3). FIG. 13C) IL-1α and GAPDH levels were determined by WB. FIG. 13D-13F) Il1a-/- mice were injected (i.v.) with B16-EV-flag or B16-IL-1α-flag stable expressing cells; FIG. 13E) representative lung pictures, FIG. 13F) tumor number per lung, (n=5). p<0.008, *p<0.0001 by Student's t test.

FIGS. 14A-14C show intracellular IL-1α reduced Akt1 activation. FIG. 14A) pAkt1 and total Akt1 in cell lysate was determined by WB. FIG. 14B) Membrane lipid strip was incubated with recombinant human proIL-1α. IL-1α was detected by ECL system. FIG. 14C) PIP3 and Na, K-ATPase levels in plasma membrane fraction were determined by WB.

DETAILED DESCRIPTION

Figure 2:
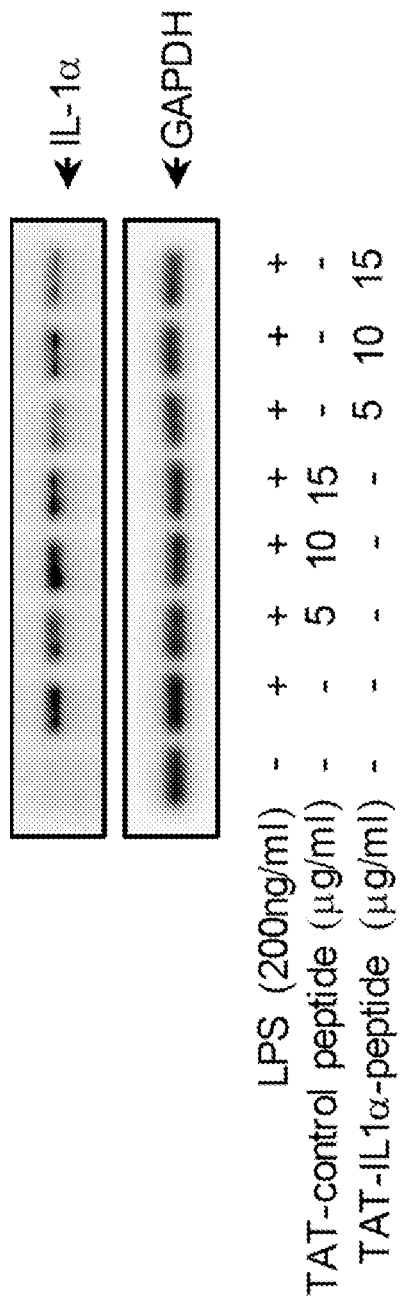
FIG. 2 depicts in accordance with various embodiments of the invention, that TAT-IL-1α peptide diminished IL-1α protein level. Peritoneal macrophages were pretreated with TAT-IL-1α or TAT-control peptides for 1 hour and stimulated with LPS (3 hours). The IL-1α protein level in cell lysate was detected by Western Blot. GAPDH was measured as a loading control.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22nd ed., Pharmaceutical Press (Sep. 15, 2012); Singleton and Sainsbury, *Dictionary of Microbiology and Molecular Biology* 3rd ed., revised ed., J. Wiley & Sons (New York, NY 2006); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

"IL-1α", "IL-1A" or "IL-1alpha" as used herein refers to Interleukin-1 alpha.

"Intracellular IL-1α" and "pro-IL-1α" are used interchangeably herein.

"IL-1α pro-piece (IAPP)" and "Short Peptide Derived from IL-1A propiece (SPDIA)" are used interchangeably herein.

"Tumor", as used herein refers to all cell growth and proliferation, whether malignant or benign, and all pre-cancerous and cancerous cells and tissues.

"Cancer", as used herein refers to or describes the physiological condition in mammals that is typically characterized by unregulated cell and/or tissue growth. Examples of cancer includes, but is not limited to lung, melanoma (such as, cutaneous, mucosal or ocular), breast, colon, head and neck cancers.

"Metastasis" as used herein refers to cancer that spreads to a different part of the body from where is started.

Terms such as "treating" or "treatment" or "to treat" or "alleviating" or "to alleviate" refer to therapeutic treatment and/or prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. Thus, those in need of treatment include those already with the disorder; those prone to have the disorder; and those in whom the disorder is to be prevented.

Terms such as "prevent" or "prevention" refer to treatment of a subject resulting in a decrease in the probability or a reduced likelihood that the subject will develop a disease or disease condition.

The term "subject" refers to any animal (e.g., a mammal), including, but not limited to humans, non-human primates, rodents, and domestic and game animals, which is to be the recipient of a particular treatment. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Typically, the terms "subject" and "patient" are used interchangeably herein in reference to a human subject. In various embodiments, a subject can be one who has been previously diagnosed with or identified as suffering from or having a condition in need of treatment. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits symptoms for a condition). A "subject in need" of treatment for a particular condition can be a subject having that condition, diagnosed as having that condition, or at risk of developing that condition.

The terms "therapeutically effective amount" or "therapeutically effective dose" or "therapeutically effective dosage" refer to an amount of a peptide, polypeptide, small molecule, or other drug effective to "treat" a disease or disorder in a subject or mammal. In the case of cancer and/or cancer metastasis, the therapeutically effective amount of the drug can reduce the severity of cancer symptoms. These include, but are not limited to, fatigue, weight loss, reduced appetite, pain, skin changes, change in bowel or bladder function, unusual bleeding, fever, nausea, vomiting, lumps or tissue masses.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (for example, unnatural amino acids, etc.), as well as other modifications known in the art.

The term "derivative" as used herein refers to a peptide that can be formed from the original peptide. In some embodiments the peptide can be formed by partial substitution of the amino acids from the original peptide. In various embodiments, the peptide has 1-6 amino acid substitutions. In various embodiments, the peptide has 1-6 amino acid substitutions. In various embodiments, the peptide has 1 amino acid substitution. In various embodiments, the peptide has 2 amino acid substitutions. In various embodiments, the peptide has 3 amino acid substitutions. In various embodiments, the peptide has 4 amino acid substitutions. In various embodiments, the peptide has 5 amino acid substitutions. In various embodiments, the peptide has 6 amino acid substitutions. In various embodiments, the amino acid substitution(s) are conservative amino acid substitution(s).

Interleukin-1 (IL-1) is a master cytokine of local and systemic inflammation, and the availability of specific IL-1-targeting agents has revealed a pathological role of IL-1α-mediated inflammation in a growing list of inflammatory diseases and cancer. The processing of IL-1α is regulated by the inflammasome and Calpain (a calcium-dependent cysteine protease). Once processed, mature IL-1α (C-terminal) binds to the cell surface receptor (R), IL-1R type 1 (IL-1RI), which is present on nearly all cells and triggers a cascade of inflammatory mediators, chemokines, and other cytokines. However, intracellular IL-1α (pro-IL-1α) is involved in many cellular functions, such as cell proliferation and expression of inflammatory cytokines, that are separate from signaling through the IL-1R. While it is known that IL-1α is phosphorylated at a serine residue in its N-terminal propiece, the mechanism of action for intracellular IL-1α in inflammation and cancer is not well understood.

As described herein, the inventors discovered a novel post-transcriptional regulatory mechanism for intracellular IL-1α, which is essential for its protein stability. Based on this finding, a peptide sequence in N-terminal pro-piece (iIL-1α-peptide), which mimics intracellular IL-1α action was developed. This peptide sequence regulates B16 melanoma cells glucose metabolism by suppressing Akt1 activation and has a protective role in cancer and metastasis. The current invention describes a short IL-1α peptide sequence and offers a therapeutic for the treatment of cancer and/or metastasis.

Metastasis is responsible for approximately 90% of all cancer-related deaths, which normally occurs in two major phases: physical translocation of a cancer cells from the primary tumor to the microenvironment of a distant tissue and then colonization within that organ. Once metastases have been established in distant tissues, current treatments frequently fail to provide durable responses. The PI3K/Akt1 signaling pathway in cancer cells has been suggested to contribute to cell survival and metastasis. Elucidating the underlying cause of metastatic inefficiency of tumor cells, and the role of contributing factors that influence the survival and tumor-initiating activity of disseminated tumor cells are important determinants of metastasis and therapeutic targets for preventing metastatic cancers.

The PI3K/Akt1 pathway is stimulated as a physiological consequence of many growth factors and regulators. Akt1 binds to PIP3 at the plasma membrane, and phosphorylated by 3-phosphoinositide-dependent kinase-1 (PDK1) and mTOR complex 2 (mTORC2). PTEN, a potent tumor suppressor, which is mutated in a large proportion of human tumors and PTEN deficient melanomas had significantly higher levels of phosphorylated Akt1. Activated Akt1 negatively regulates the function or expression of several pro-apoptotic proteins such as caspase-9, GSK3, BH3-only protein BAD. Akt1 signaling is strongly related to cell survival through its roles in nutrient uptake and metabolism and the maintenance of mitochondrial membrane potential and glycolysis. Akt1 was shown to stimulate the association of hexokinase isoforms with the mitochondria, where they more readily phosphorylate glucose. Activation of the PI3K/Akt1 pathway results in a disturbance of control of cell growth and survival, which contributes to a competitive growth advantage, metastatic competence and, frequently, therapy resistance. This pathway is therefore an attractive target for the development of novel anticancer agents.

Crosstalk between tumor cells and their microenvironment is facilitated by a variety of cytokines and chemokines. Interleukin-1 (IL-1) is a master cytokine linked with broad spectrum of diseases including cancer. There are two related but distinct IL-1 genes, Il1α and Il1β, encoding IL-1α and IL-1β, respectively. The precursor (pro) of IL-1α and IL-1β is cleaved into C-terminal secreted form and N-terminal pro-piece by different inflammatory proteases, but their secreted forms bind to the same cell surface receptor, IL1 receptor type 1 (IL-1RI) and trigger inflammatory signaling cascade, which is associated with malignant tumor growth. ProIL-1α in cancer cells has a subcellular localization. The present application provides data showing that a paradigm shifting role of proIL-1α has been discovered.

Cells communicate and exchange information by many different mechanisms such as secreted growth factors, cytokines, chemokines and nanotubules. One of the earliest cell-to-cell communication mechanisms in development involves spherical membrane fragments shed from the cell surface or the endosomal compartment by extracellular microvesicles (ExMVs). While larger ExMVs (~100 nm-1 μm) are shed from lipid raft-enriched cell surface membrane domains by blebbing and budding of the cell membrane, smaller ExMVs (~40-150 nm), also known as exosomes, are derived from the endosomal cell membrane compartment and originate from the release of Golgi apparatus derived vesicles. Many different cells including tumor cells are capable of secreting both ExMVs and exosomes. The ExMVs can transfer mRNA, miRNA, and large non-coding RNA molecules in addition to proteins, bioactive lipids, metabolites, and signaling nucleotides between cells in a horizontal manner. The ExMVs may also be employed in producing anti-tumor vaccines.

The B16 (also referred herein as "B16F10") mouse melanoma metastasis model is widely accepted, as B16 cells injected via tail vein reliably colonize the lungs, with easily identifiable tumors after 7-14 days. While the use of a genetic melanoma model may be ideal, it requires the use of immunodeficient mice or the complicated and expensive humanized mice. While the B16 model may have its known caveats, it has repeatedly given very useful novel mechanistic clues that can be further tested in more relevant models, such as genetically engineered mice. In addition to the B16 model, a mouse melanoma cell line with human genetic drivers that are more relevant to human melanoma formation and progression were also used. To this effect, a non-immunogenic cell line (YUMM1.7) was used. In the YUMM1.7 cells, nearly 50% of human melanomas harbor a gain of function in the Braf$^{V600E}$ Cdkn2a-/- Pten-/- mutations and they form reliable lung tumors following tail vein injection (5×10$^5$, in 3 weeks). Other common mutations in human melanoma include CDKN2A (familial melanoma gene), inactivation of tumor suppressors including INK4A, ARF, p53, and PTEN, as well as mutations in proto-oncogenes such as H-RAS, N-RAS, and K-RAS.

The data indicates that when host-derived pro-IL-1α is transferred into B16 cells during melanoma colonization in the lungs, tumor burden and metastatic potential of B16 cells was reduced, by regulating Akt1 activation and glycolysis. Additionally, the use of "YUMM1.7," the murine cell line harboring relevant human mutations, makes these results more translational. Based on these new findings, a Short Peptide Derived from IL-1A propiece (SPDIA) was designed, as a novel therapeutic agent, which does not contain the IL-1α receptor signaling sequence. SPDIA significantly reduced Akt1 activation and glycolysis in melanoma cells and exhibited protective effects in vivo using a YUMM1.7 subcutaneous melanoma model.

The present invention is based, at least in part, on these findings. The present invention addresses the need in the art for a treatment for cancer and/or metastasis and uses a peptide designed from the N-terminal IL-1α pro-piece. Related polypeptides and compositions comprising a pro-IL-1α peptide, a pro-IL-1α peptide mimic, IL-1α pro-piece peptide, and methods of using the pro-IL-1α peptide, a pro-IL-1α peptide mimic, and IL-1α pro-piece for the treatment of cancer and/or metastasis are also provided.

Methods of Treating, Preventing and/or Ameliorating Cancer and/or Cancer Metastasis Various embodiments of the present invention provide for a method of treating cancer in a subject in need thereof.

Various embodiments of the present invention provide for a method of preventing and/or reducing the likelihood of having cancer in a subject in need thereof.

Various embodiments of the present invention provide for a method of ameliorating cancer or symptoms of cancer in a subject in need thereof.

In various embodiment, the method comprises administering a therapeutically effective dose of a pro-IL-1α peptide, a pro-IL-1α peptide mimic or both. In various embodiments, the method comprises administering a therapeutically effective dose of an IL-1α pro-piece peptide.

In various embodiments, the method comprises providing a composition comprising a pro-IL-1α peptide, a pro-IL-1α peptide mimic, or both; and administering a therapeutically effective dose of the composition comprising the pro-IL-1α peptide, the pro-IL-1α peptide mimic, or both thereof to the subject.

In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

In various embodiments, the cancer is melanoma and/or lung cancer. In particular embodiments, the cancer is melanoma. In various particular embodiments, the cancer is metastatic melanoma. In various particular embodiments, the cancer the metastatic melanoma in the lung. In particular, various embodiments, the cancer is lung cancer.

In various other embodiments, treating and/or ameliorating cancer or a symptom of cancer in a subject result in reduced tumor burden. In yet other embodiments, the reduced tumor burden comprises a reduced tumor volume and/or tumor mass. In other embodiments, the reduced tumor burden comprises a reduced number of cancer cells. In yet other embodiments, the reduced tumor burden comprises a reduction in the amount of cancer in the subject's body. "Amount of cancer" as used herein can refer to the total number of cancer cells or size of one or more tumors in the subject's body.

In various other embodiments, treating and/or ameliorating cancer or a symptom of cancer in a subject result in slowing the growth of a tumor. In various other embodiments, treating and/or ameliorating cancer or a symptom of cancer inhibits the tumor's or cancer cells' growth and/or ability to multiply.

In various embodiments, administering a therapeutically effective dosage of the composition comprising a pro-IL-1α peptide, a pro-IL-1α peptide mimic or both reduces Akt1 activation and glycolysis in the cancer cells. In various embodiments, the pro-IL-1α peptide mimic is a IL-1α pro-piece peptide. In various embodiments, the IL-1α pro-piece peptide comprises a peptide having SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%. In various other embodiments, AKT1 phosphorylation is reduced. In yet other embodiments, the glycolic rate is decreased.

In various other embodiments, melanoma, metastatic melanoma, melanoma that has metastasized to the lung and/or lung cancer is treated, prevented, and/or ameliorated, and/or the likelihood of having melanoma, metastatic melanoma, melanoma that has metastasized to the lung and/or lung cancer is reduced when the pro-IL-1α peptide, a pro-IL-1α peptide mimic or both is administered. For example, when a IL-1α pro-piece peptide comprises a peptide having SEQ ID NO:1 is administered.

Various embodiments of the present invention also provide for a method for reducing, preventing, or reducing the likelihood of cancer metastasis in a subject in need thereof, comprising administering a therapeutically effective dosage of a pro-IL-1α peptide, a pro-IL-1α peptide mimic or both to the subject. In various embodiments, the pro-IL-1α peptide, a pro-IL-1α peptide mimic or both is provided in a composition. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

Various embodiments of the present invention also provide for a method for reducing, preventing, or reducing the likelihood of cancer metastasis in a subject in need thereof, comprising providing a pro-IL-1α peptide, a pro-IL-1α peptide mimic or both; and administering a therapeutically effective dosage of the pro-IL-1α peptide, a pro-IL-1α peptide mimic or both to the subject. In various embodiments, the pro-IL-1α peptide, a pro-IL-1α peptide mimic or both is provided in a composition. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

In various embodiments, administering a therapeutically effective dosage of a pro-IL-1α peptide, a pro-IL-1α peptide mimic or both reduces Akt1 activation and glycolysis in the cancer cells. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%. In various other embodiments, AKT1 phosphorylation is reduced. In yet other embodiments, the glycolic rate is decreased. In various other embodiments, melanoma and/or lung cancer metastasis is reduced or prevented when the pro-IL-1α peptide, a pro-IL-1α peptide mimic or both is administered. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

Various embodiments of the present invention also provide for a method, comprising providing a composition comprising a pro-IL-1α peptide, a pro-IL-1α peptide mimic or both; and administering a therapeutically effective amount of the composition to a subject in need of treating cancer and/or cancer metastasis. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

In various embodiments, the cancer is melanoma and/or lung cancer. In various other embodiments, lung and/or melanoma metastasis is reduced or prevented. In other embodiments, administering the composition comprising a IL pro-IL-1α peptide, a pro-IL-1α peptide mimic or both reduces tumor burden. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%. In yet other embodiments, reduced tumor burden comprises a reduced tumor volume and/or tumor mass. In various embodiments, administering the composition comprising a pro-IL-1α peptide, a pro-IL-1α peptide mimic or both reduces Akt1 activation and glycolysis in the cancer cells. In various other embodiments, AKT1 phosphorylation is reduced. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%. In yet other embodiments, glycolic rate is decreased.

Examples of cancer includes, but is not limited to lung, melanoma (such as, cutaneous, mucosal or ocular), breast, colon, head and neck cancers.

In various embodiments, the peptide comprises one or more peptides as represented by SEQ ID Nos. 1-4 (See Table 1). In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

In various embodiments, the pro-IL-1α peptide mimic consists of one or more of peptides as represented by SEQ ID Nos. 1-4. In various embodiments, the pro-IL-1α peptide mimic consists of a peptide as represented by SEQ ID NO:1. In various embodiments, the IL-1α pro-piece peptide consists of a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

The Short Peptide Derived from IL-1A propiece (SPDIA) has marked differences from IL-1α. ProIL-1α is cleaved into the C-terminal secreted form and an N-terminal pro-piece by inflammatory proteases. The secreted form of IL-1α in the tumor microenvironment is associated with a more metastatic tumor phenotype. However, SPDIA imparts anti-cancer and anti-cancer metastasis as discussed herein. SPDIA is cell soluble and is able to penetrate into cell.

TABLE 1

IL-1α Sequences

| Peptide Name | Sequence | SEQ ID NO |
|---|---|---|
| IL-1α pro-piece (SPDIA Peptide) | GKVLKKRRLSL | 1 |
| Human IL-1α consensus sequence | TSSNGKILKKR RLSFSET | 2 |
| TAT-IL-1α-peptide | YGRKKRRQRRR LKKRRLSL | 3 |
| Mouse IL-1α | ATSSNGKILKK RRLSFS | 4 |

Pharmaceutical Compositions, Administration and Dosage

Various embodiments of the present invention provide for a pharmaceutical composition, comprising a therapeutically effective amount of a pro-IL-1α peptide, a pro-IL-1α peptide mimic or both, or a derivative, and/or salt thereof; and a pharmaceutically acceptable carrier or a pharmaceutically acceptable excipient, or both. In various embodiments, the pro-IL-1α peptide mimic is a IL-1α pro-piece peptide. In various embodiments, the IL-1α pro-piece peptide comprises a peptide as represented by SEQ ID NO:1. In various embodiments, the IL-1α pro-piece peptide comprises a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%. In various embodiments, the pro-IL-1α peptide mimic comprises or consists of one or more peptides as represented by SEQ ID Nos. 1-4. In various embodiments, the pro-IL-1α peptide mimic comprises or consists of a peptide as represented by SEQ ID NO:1. In various embodiments, the IL-1α pro-piece peptide comprises or consists of a peptide as represented by SEQ ID NO:1, but with 1, 2, or 3 amino acid substitutions, deletions, or additions. In various embodiments, the 1, 2, or 3 amino acid substitutions is conservative amino acid substitutions. In various embodiments, the 1, 2, or 3 amino acid deletions or additions result in preserving at least 70, 80, 90, 95, 96, 97, 98, 99% efficacy of SEQ ID NO:1, or increasing the efficacy of SEQ ID NO:1 by at least 1, 2, 3, 4, 5, 10, 20, 30, 40, 50, 75, 100, 150, 200%.

In various embodiments, the composition comprises a pharmaceutically acceptable carrier. In various embodiments, the composition comprises a pharmaceutically acceptable excipient. In various other embodiments, the composition comprises a pharmaceutically acceptable carrier and a pharmaceutically acceptable excipient. In various embodiments, the pharmaceutically acceptable carrier the pharmaceutically acceptable excipient is an agent that stabilizes the pro-IL-1α peptide, or pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or preserves the efficacy of the pro-IL-1α peptide, or the pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions). In various embodiments, the pharmaceutically acceptable carrier the pharmaceutically acceptable excipient is an agent that aid in the delivery of the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) to its intended location.

The pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) of the invention is useful in a variety of applications including, but not limited to, therapeutic treatment methods, such as the treatment of cancer and/or cancer metastasis. The methods of use may be in vitro or in vivo methods. In certain embodiments, the IL-1α pro-piece peptide is an intracellular IL-1α mimic (pro-IL-1α peptide mimic).

In certain embodiments, the cancer treated with the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) is lung cancer or melanoma. In some embodiments, cancer metastasis to the lungs is prevented or reduced.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, intratracheally or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

In various embodiments, an agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intratracheally, intracavity, and can be delivered by peristaltic means, if desired, or by other means known by those skilled in the art. In particular embodiments, compounds used herein are administered orally, intravenously or intramuscularly to a patient having cancer and/or cancer metastasis. In certain embodiments, the compounds used herein are administered orally, intravenously or intramuscularly to a patient having lung cancer and/or melanoma. In certain other embodiments, the compounds used herein are administered orally, intravenously or intramuscularly to a patient having cancer metastasis to the lungs.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, the present invention provides pharmaceutical compositions including a pharmaceutically acceptable excipient along with a therapeutically effective amount of the IL-1α pro-piece peptide (or IL-1α pro-piece peptide as represented by SEQ ID NO:1, but with 1, 2, or 3 amino acid substitutions, deletions, or additions). "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in the therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent used in the invention that will be effective in the treatment of a particular disorder or condition will depend on the nature of the disorder or condition, and can be determined by one of skill in the art with standard clinical techniques.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical composition according to the invention can be prepared to contain any combination of adjuvants, carriers and/or excipients, as would be deemed beneficial by one of skill in the art. In various embodiments, the pharmaceutical composition comprises the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and one or more adjuvants. In various other embodiments, the pharmaceutical composition comprises the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and one or more carriers. In yet other embodiments, the pharmaceutical composition comprises the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and one or more excipients. In various other embodiments, the pharmaceutical composition comprises the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and one or more adjuvants and one or more carriers. In other embodiments, the pharmaceutical composition comprises the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both one or more adjuvants and one or more excipients. In certain embodiments, the pharmaceutical composition comprises the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and one or more carriers and one or more excipients. In some embodiments, the pharmaceutical composition comprises the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and one or more adjuvants, one or more carriers and one or more excipients.

In various embodiments, the pharmaceutical composition comprises of pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and a pharmaceutically acceptable carrier. In various embodiments, the pharmaceutically acceptable carrier comprises a cream, emulsion, gel, liposome, nanoparticle, or ointment. In various embodiments, the pharmaceutical composition is a fusion protein comprising the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and another protein or peptide. The other protein or peptide can provide the pharmaceutical composition with characteristics such as enabling cell targeting, protein stability, increased binding to protein or nucleic acid targets, provide additional therapeutic effects (such as, but not limited to, analgesics and/or anti-inflammatory agents), and labeling of the pharmaceutical composition to identify the composition and/or ultimate target in the body (e.g., tissues, organs, cells).

PEGylation is the coupling of polyethylene glycol (PEG) to a biologically active agent (e.g., proteins and antibody fragments). In various embodiments, the pharmaceutical composition comprises of the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both and a PEG molecule. In some embodiments, the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both can be covalently coupled to the PEG molecule. In other embodiments, the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both can be covalently coupled to the PEG molecule via a functional group of the IL-1α pro-piece peptide.

In various embodiments, the PEG molecule comprises of different chain lengths and molecular weights. In other embodiments, the PEG molecule might be either linear or branched. In various other embodiments, the covalent coupling of the IL-1α pro-piece peptide and the PEG molecule occurs at the N-Terminus, C-terminus or at an additional amino acid within the IL-1α pro-piece peptide. In yet other embodiments, multiple peptides are bound to the PEG molecule. In some embodiments, peptides of the same or different amino acid sequence are bound to the PEG molecule. In other embodiments, the PEG molecule has a molecular weight ranging between 2 and 100 kDa. In some embodiments, the PEG molecules molecular weight range is 2-10 kDa, 10-20 kDa, 20-30 kDa, 30-40 kDa, 40-50 kDa, 50-60 kDa, 60-70 kDa, 70-80 kDa, 80-90 kDa, or 90-100 kDa.

Examples of PEGs include, but are not limited to heterobifunctional PEGs (such as, azide (-N3), biotin, maleimide, NHS ester, thiol, COOH, Amine, hydroxyl and acrylate/methacrylate functionalized), homobifunctional PEGs, Monofunctional PEGs, PEG Dendrimers and Multi-arm PEGs, and PEG Copolymers (miniPEGs). In various embodiments, the miniPEG is a diethylene glycol.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of an effective pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both can be as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biological samples obtained, or the responses observed in the appropriate animal models.

For the treatment of the disease, the appropriate dosage of the IL-1α pro-piece peptide or mimic (e.g., peptides as represented by SEQ ID Nos. 1-4, IL-1α pro-piece peptide as represented by SEQ ID NO:1, but with 1, 2, or 3 amino acid substitutions, deletions, or additions) of the present invention depends on the type of cancer to be treated, the severity and course of the disease, the responsiveness of the disease, whether the peptide is administered for therapeutic or preventative purposes, previous therapy, and patient's clinical history. The dosage can also be adjusted by the individual physician in the event of any complication and at the discretion of the treating physician. The IL-1α pro-piece peptide or mimic can be administered one time or over a series of treatments lasting from several days to several months, or until a cure is effected or a diminution of the disease state is achieved (e.g., treatment or amelioration of cancer and/or cancer metastasis). The duration of treatment depends upon the subject's clinical progress and responsiveness to therapy. In certain embodiments, dosage is from 0.01 μg to 100 mg per kg of body weight, and can be given once or more daily, weekly, monthly or yearly. For systemic administration, subjects can be administered a therapeutic amount, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Kits

The present invention is also directed to a kit to treat cancer and/or cancer metastasis. In various embodiments, the kit treats lung cancer and/or melanoma. In other embodiments, the kit prevents and/or reduces cancer metastasis to the lungs. The kit comprises of the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both described herein, which can be used to perform the methods described herein. The kit is useful for practicing the inventive method of providing treatment to a cancer patient by administering the IL-1α pro-piece peptide. The kit is also useful for practicing the inventive method of providing treatment to a patient with cancer metastasis by administering the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both. The kit is an assemblage of materials or components, including at least one of the inventive compositions. Thus, in some embodiments the kit contains a composition including the pro-IL-1α peptide, a pro-IL-1α peptide mimic (e.g., IL-1α pro-piece peptides, peptides as represented by SEQ ID Nos. 1-4, IL-1α pro-piece peptide as represented by SEQ ID NO:1, but with 1, 2, or 3 amino acid substitutions, deletions, or additions) or both, for the treatment of cancer and/or cancer metastasis, as described above.

The exact nature of the components configured in the inventive kit depends on its intended purpose. For example, some embodiments are configured for the purpose of treating cancer and/or cancer metastasis. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat, alleviate, reduce or prevent cancer and/or cancer metastasis. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of an inventive composition containing the IL-1α pro-piece peptide and one or more pharmaceutically acceptable carriers, excipients, and/or adjuvants. The packaging material generally has an external label which indicates the contents and/or purpose of the kit and/or its components.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1

Human IL-1α is phosphorylated at the serine 87 (S87) residue (mouse equivalent to S90) of the N-terminal pro-piece by protein kinase A (PKA). The sequence for human IL-1α (N-terminal--TSSNGKILKKRRLSFSET--C-terminal (SEQ ID NO: 2)) possesses the consensus sequence "KKRRLS" (SEQ ID NO: 5) of ABC-family kinases. IL-1α phosphorylation is required for its membrane localization. A mutant IL-1α plasmid cDNA was made for studying the role of IL-1α subcellular localization: the Serine at 87 was exchanged with Alanine (S87A) using the QuikChange Site-Directed Mutagenesis kit, Cat #200518 and human pCMV-IL-1α-flag plasmid DNA (Sino Biological Inc. Cat #HG10128-M-F). Primers were designed by the QuikChange Primer Design software program.

Wild-type (WT)-IL-1α or mutant S87A-IL-1α plasmid was transfected into 293 cells and stable expressing cells lines were made. These cells express similar levels of IL-1α mRNA (FIG. 1A). IL-1α protein was detected only in WT-IL-1α transfected cells but not mutant S87A-IL-1α transfected cells (FIG. 1B). However, S87A-IL-1α protein was clearly detected in the presence of MG132, a proteasome inhibitor (FIG. 1C), suggesting that IL-1α serine phosphorylation is important for its protein stability. Based on this finding, a pseudosubstrate peptide was made to inhibit IL-1α phosphorylation, which may provide a more convenient way to control IL-1α during inflammation. A IL-1α short peptide (YGRKKRRQRRR-LKKRRLSL, SEQ ID NO: 3), which contains the ABC family kinase motif (LKKRRLSL, SEQ ID NO: 6) and TAT peptide sequence (YGRKKRRQRRR, SEQ ID NO: 7) was designed. The TAT peptide allows for cell penetration. The peptides ordered were TAT-IL-1α peptide: YGRKKRRQRRRLKKRRLSL (SEQ ID NO: 3) and TAT-Control peptide: YGRKKRRQRRRLAKARLAL (SEQ ID NO: 8)—Creative Dynamics Inc.).

The inventors investigated whether TAT-IL-1α peptide triggers IL-1α protein degradation by reducing its serine phosphorylation. Peritoneal macrophages were pretreated with TAT-IL-1α or TAT-Control peptides for 1 hour, stimulated with LPS, and the IL-1α protein level in whole cell lysate was detected by western blot (WB) (FIG. 2). The IL-1α protein level was decreased in TAT-IL-1α treated cells. However, TAT-Control peptide also slightly decreased IL-1α protein level compared to LPS alone, demonstrating that TAT-peptide or LPS treatment may affect this system.

Figure 3:
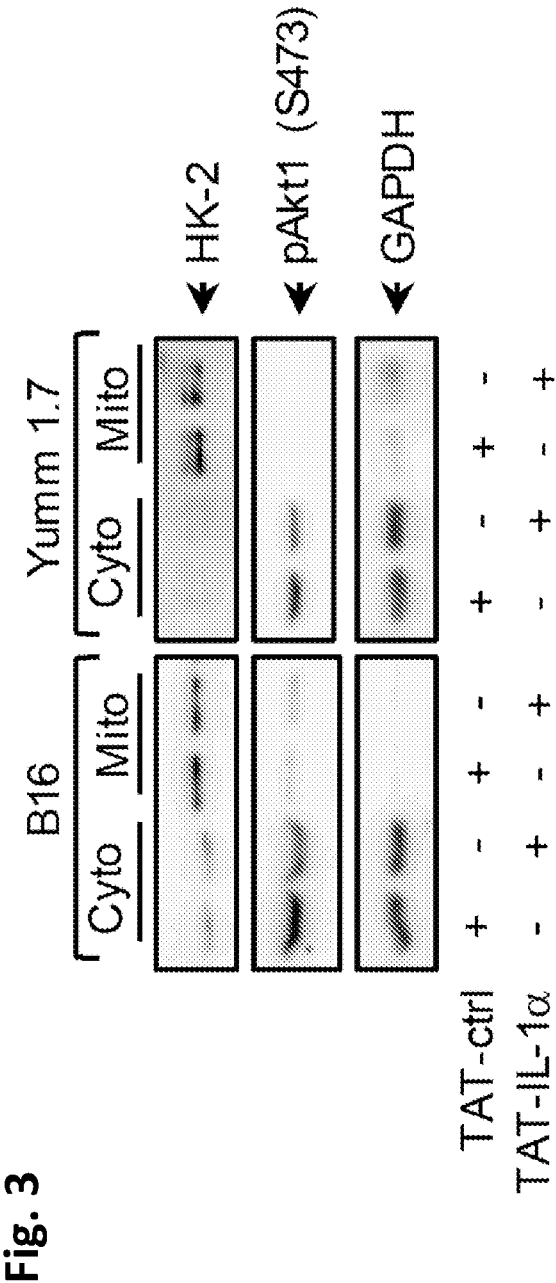
FIG. 3 depicts in accordance with various embodiments of the invention, that TAT-IL-1α peptide diminished Akt1 activation and increased HK-2 mitochondrial dissociation. B16 or Yumm 1.7 murine melanoma cells were treated with TAT-IL-1α (40 μg/ml) or TAT-Control peptide for 5 hours. HK-2 level and pAkt1 activation in the cytosolic and mitochondrial fraction were detected by Western Blot. GAPDH was measured as a loading control.

Next, the inventors checked whether TAT-IL-1α peptide regulates Akt1 activation, because it has an Akt1 consensus motif. LPS stimulation is required for Akt1 activation in macrophages. However, Akt1 is constitutively activated in many tumor cells. Therefore, B16 and Yumm 1.7 murine melanoma cancer cells were selected for these experiments. The B16 or Yumm 1.7 cells were treated with TAT-IL-1α or TAT-Control peptide (at a higher dose than used previously for macrophages) for 5 hours (FIG. 3). Interestingly, TAT-IL-1α significantly inhibited Akt1 activation. Akt1 is a responsible kinase for hexokinase 2 (HK-2) phosphorylation, which is enhanced in mitochondrial translocation. Consistent with this, HK-2 mitochondrial translocation was also diminished in TAT-IL-1α treatment compared to TAT- Control (FIG. 3). Without being bound to any particular theory, this suggests that TAT-IL-1α peptide may be a potent inhibitor of Akt1 activation.

Figure 4A:
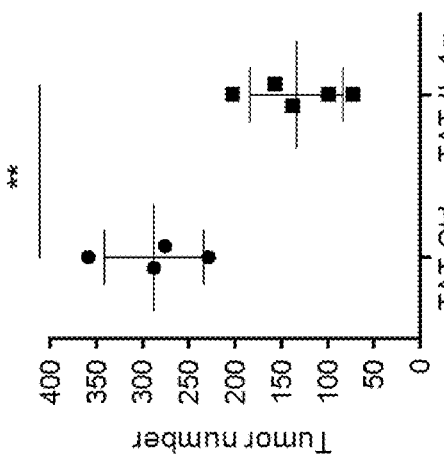
FIGS. 4A-4C depict in accordance with various embodiments of the invention, that TAT-IL-1α peptide reduced lung metastasis.
Figure 4B:
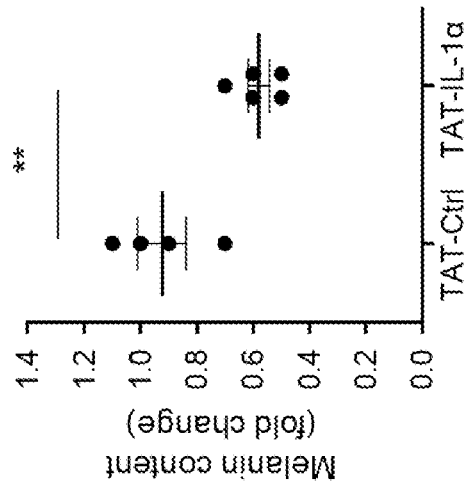
Figure 4C:
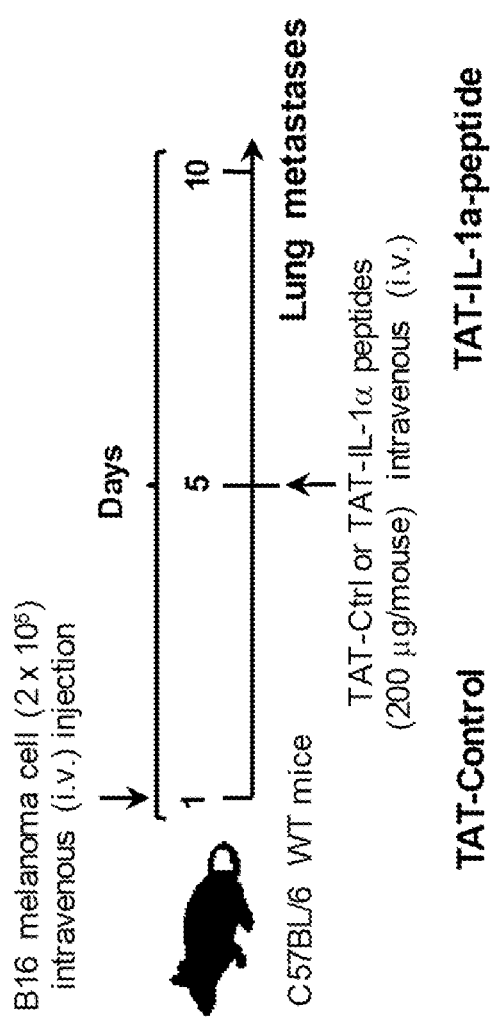
Figure 4C:
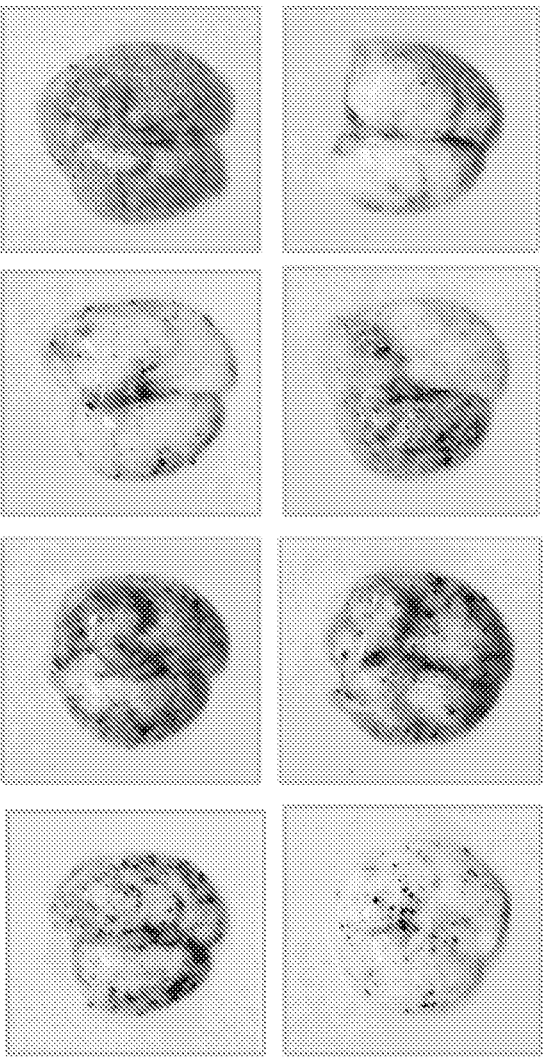
Figure 5A:
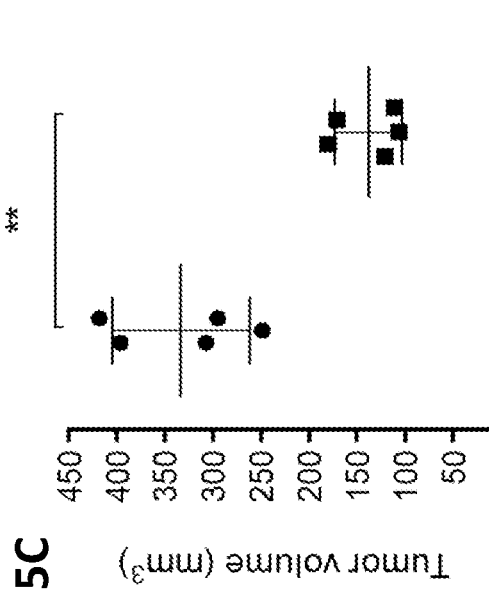
FIGS. 5A-5D depict in accordance with various embodiments of the invention, that iIL-1α-peptide decreased tumor development.
Figure 5B:
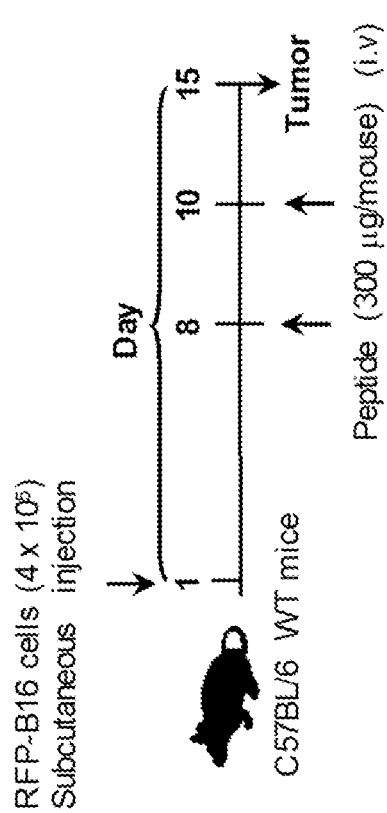
Figure 5C:
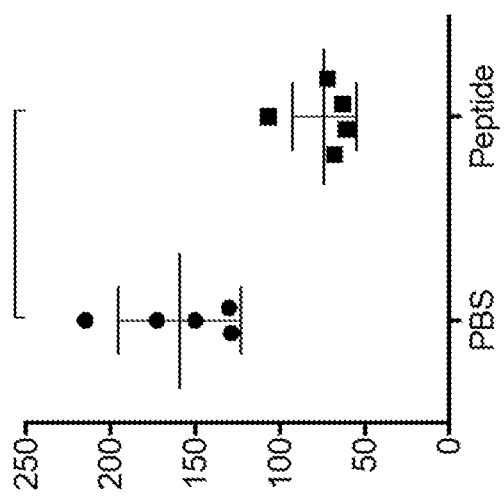
Figure 5D:
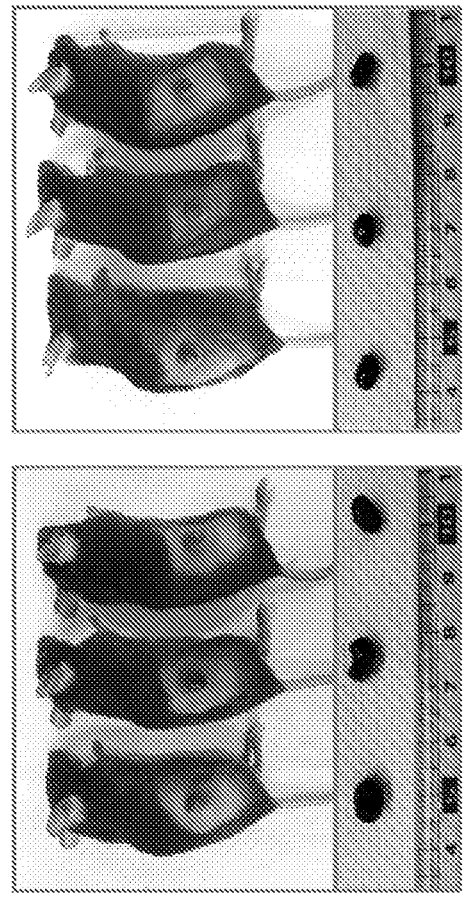

The peptides were subsequently tested in vivo. B16 melanoma cells were intravenously (i.v.) injected in the tail vein of female WT mice. Five days later, TAT-IL-1α or TAT-Control peptide was injected in the tail vein (i.v.). Five days post treatment, lungs were harvested and examined for metastasis. TAT-IL-1α treatment significantly reduced melanoma metastasis (FIG. 4A). The tumor number and melanin content were diminished in the TAT-IL-1α treatment group compared to TAT-Control peptide treatment. (FIGS. 4B and 4C). Without being bound to any particular theory, these data suggest that TAT-IL-1α peptide may have a protective role for B16 induced melanoma metastasis.

TAT protein upregulates expression of IL-6 and IL-8 in human breast cancer cells by the NF-kB dependent pathway. Human IL-1α short peptide (nuclear localization sequence) can deliver macromolecules in vitro and in vivo. Therefore, the peptide was redesigned to include the nuclear localization sequence and the ABC family kinase consensus motif. The intracellular IL-1α mimic peptide (iIL-1α-peptide or IL-1α pro-piece) sequence designed is GKVLKKRRLSL (SEQ ID NO: 1) and was ordered from Genscript USA Inc.

This peptide was used in an in vivo model, where WT mice were injected subcutaneously (subQ) with B16 cells. Eight days later, tumors were measured and iIL-1α-peptide was injected intravenously on days 8 and 10 in the tail vein. PBS was injected in the control group. On day 15, mice were sacrificed and tumors were examined (FIG. 5). The iIL-1α-peptide reduced tumor volume and mass compared to the control group. Without being bound to any particular theory, this suggests that the iIL-1α-peptide may have a protective role against B16 melanoma cancer.

Figures 10A, 10B, 10C:
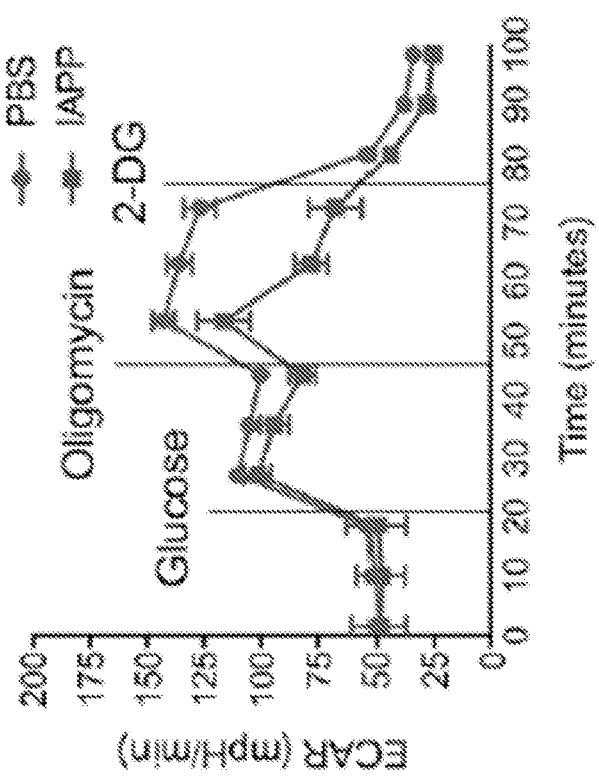
FIGS. 10A-10C depict in accordance with various embodiments of the invention, the iIL-1α-peptide reduces Akt1 activation and glycolysis in melanoma cells. B16 cells isolated from tumors from WT mice were treated with iIL-1α-mimic peptide (iIL-1α-peptide) (40 μg/ml) or PBS for 5 hours.

B16 cells were isolated from WT mice and cultured in-vitro. The cells were treated with the iIL-1α-mimic peptide (iIL-1α peptide) or PBS for 5 hours (FIG. 10). The iIL-1α-mimic peptide significantly inhibited Akt1 activation and HK-2 mitochondrial translocation (FIG. 10B). Consistent with these results, iIL-1α reduced extracellular acidification rate (ECAR) (FIG. 10C). Without being bound to any particular theory, the data demonstrate that iIL-1α-mimic peptide may be a potent Akt1 inhibitor and have an anticancer effect.

IL-1α has a Protective Role Against B16 Melanoma

Figure 6A:
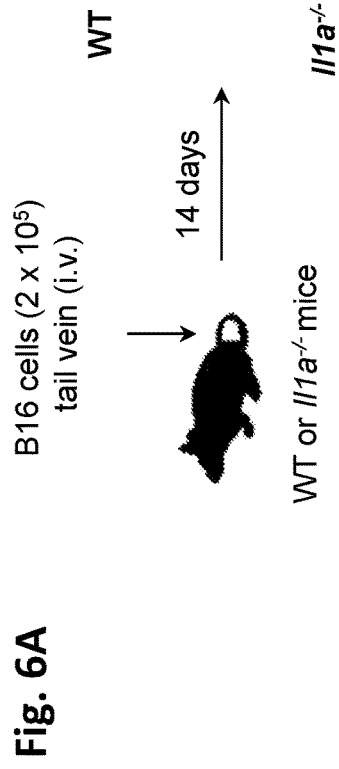
FIGS. 6A-6E depict in accordance with various embodiments of the invention, that IL-1α$^{-/-}$ mice are susceptible to metastasis. Female WT or IL-1α$^{-/-}$ mice were injected (i.v.) with B16 melanoma cells and lungs were harvested 14 days later. B16 cells developed increased tumor burden in IL-1α$^{-/-}$ mice compared with WT mice.
Figure 6B:
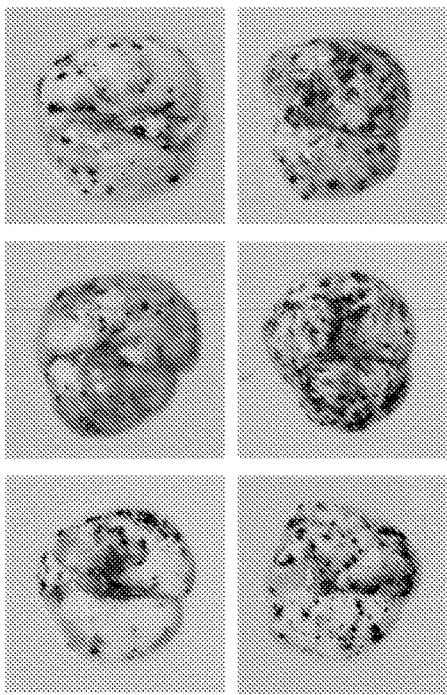
Figure 6B:
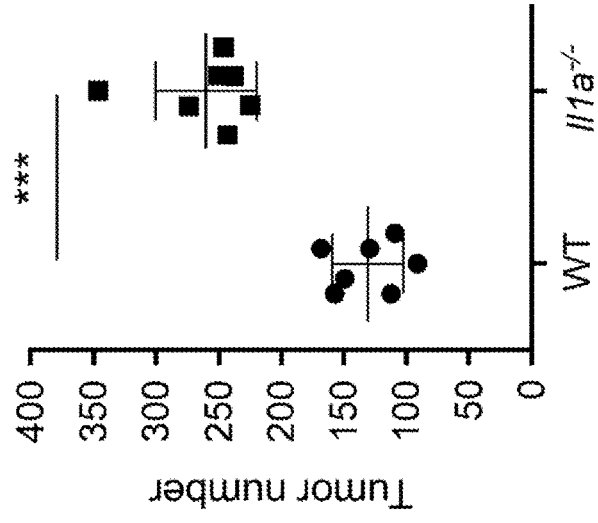
Figure 6C:
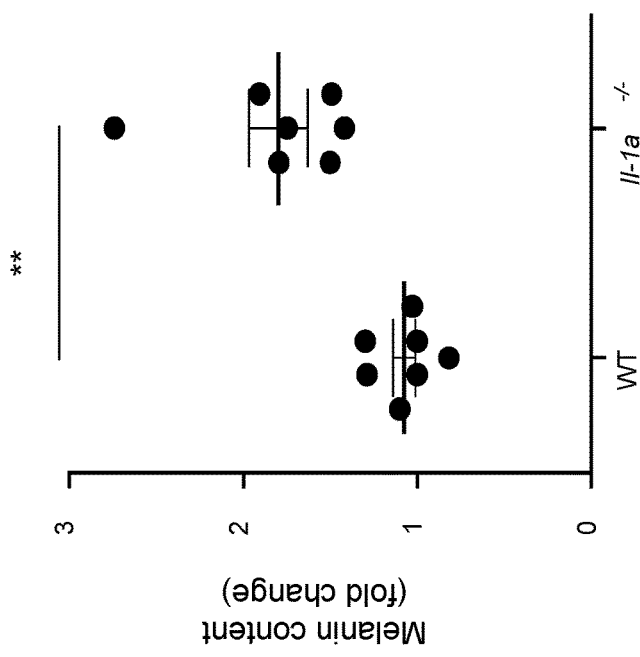
Figure 6E:
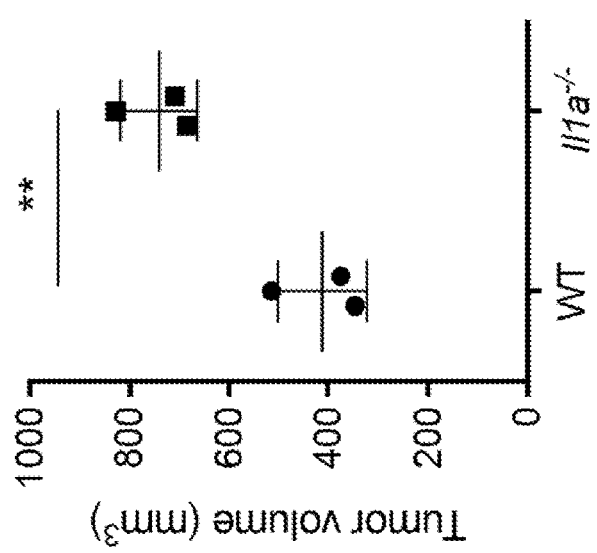

Interleukin-1 (IL-1) is a master cytokine controlling local and systemic inflammation, and the availability of specific IL-1-targeting agents has revealed a pathological role of IL-1-mediated inflammation in a growing list of inflammatory diseases and cancer. However, membrane IL-1α may also have an anticancer effect. B16 cells were intravenously injected in the tail vein of WT or IL-1α-/- mice and lungs were harvested and examined for metastasis 14 days later (FIG. 6A). Higher tumor and melanin content were observed in IL-1α-/- mice compared to WT mice (FIGS. 6B and 6C). Without being bound to any particular theory, these data suggest that IL-1α may have a protective role against lung metastasis.

Next, the inventors investigated whether IL-1α directly affects the B16 melanoma cells during cancer development. For these experiments, Red Fluorescence Protein (RFP) stable expressing B16 cells (B16-RFP) were made (FIG. 7), which allows for the isolation of B16 cells from metastatic lungs. B16-RFP cells were intravenously (i.v.) injected in the tail vein of WT or IL-1α-/- mice and RFP positive cells (B16) were sorted from metastatic lungs by using the flow cytometer (Cell sorter Canto II), 14 days later (FIG. 8A). Interestingly, Akt1 activation and ECAR is significantly higher in B16-RFP cells obtained from metastatic lungs of IL-1α-/- mice compered to WT controls (FIGS. 8B and 8C). Thus, without being bound to any particular theory, this data demonstrates that intracellular IL-1α suppresses lung metastasis by directly affecting B16 melanoma cell metabolism.

Example 2

The mouse models used were C57Bl/6 WT or Il1α-/- mice injected with B16 cells ($2\times10^5$ tail vein), ($3\times10^5$ subcutaneous) or C57Bl/6 WT mice injected with YUMM1.7 cells ($5\times10^5$ subcutaneous). The IL-1α, pAkt1 and HK-2 levels were determined by WB. The glycolytic rate in B16 cells was measured by Seahorse.

Statistics: For data involving single comparisons, a 2-tailed unpaired Student's t-test was used. For non-parametric data, the Mann-Whitney T-test is used. For multiple comparison test, significance is evaluated by one or two-way ANOVA with Tukey's post-hoc test where appropriate. In all animal experiments, n=15.

Figure 6D:
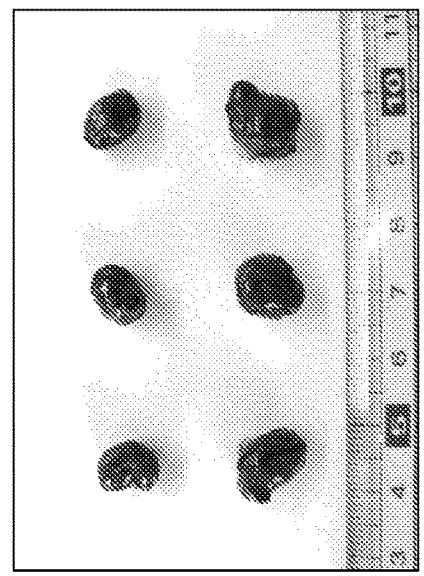
Figure 6D:
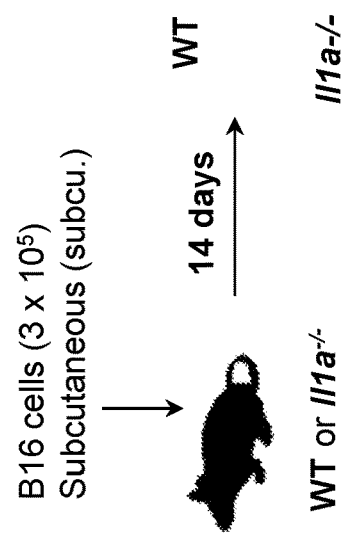

B16 cells developed increased tumor burden in IL1α-/- mice compared with WT mice. We injected (i.v.) B16 cells into WT or IL1α-/- mice at 7-8 weeks of age, and observed that IL1α-/- mice had increased tumor burden in the lungs when compared with WT mice (FIGS. 6A and 6B). Subcutaneous injection with B16 cells also developed larger cutaneous melanoma tumors in IL1α-/- mice compared with WT mice (FIGS. 6C and 6D). Without being bound to any particular theory, these data suggest that host IL-1α may have a protective role against melanoma tumor burden.

Figure 13C:
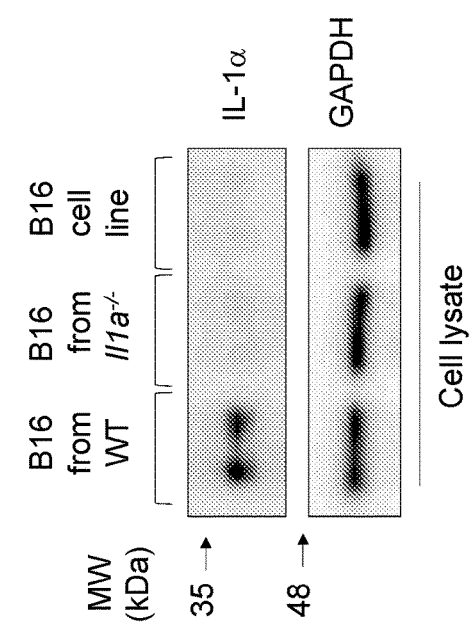
FIGS. 13A-13F show intracellular proIL-1α regulates melanoma colonization in the lungs. A-C) B16-RFP cells were isolated from metastatic lungs of WT or Il1a-/- mice and injected (i.v.) into WT mice.
Figure 13B:
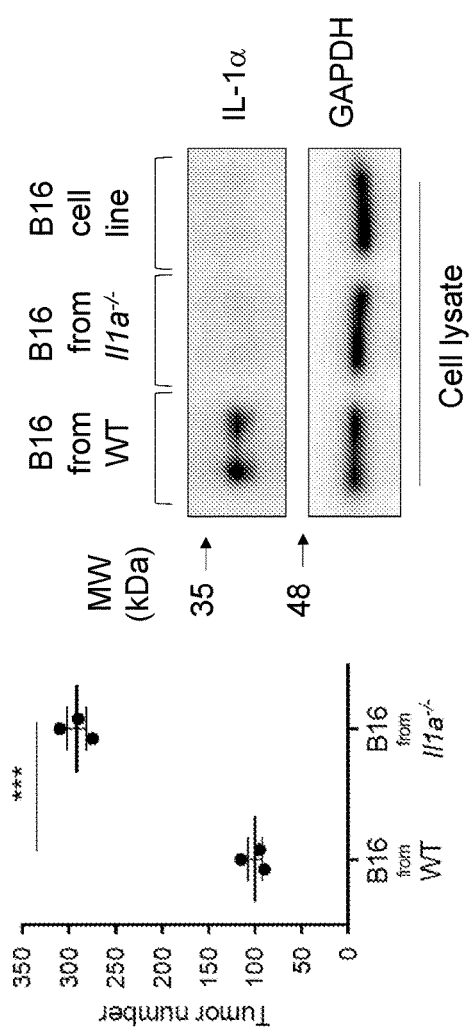
Figure 13A:
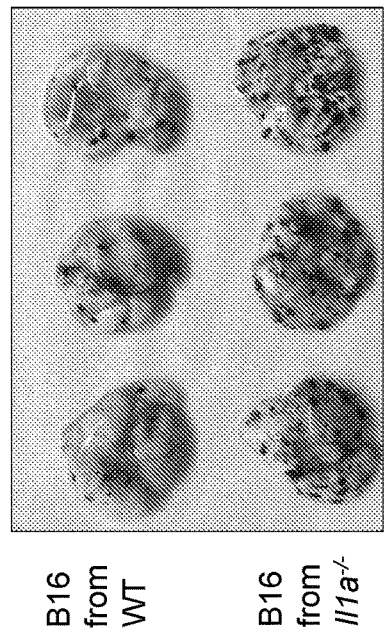
Figure 13F:
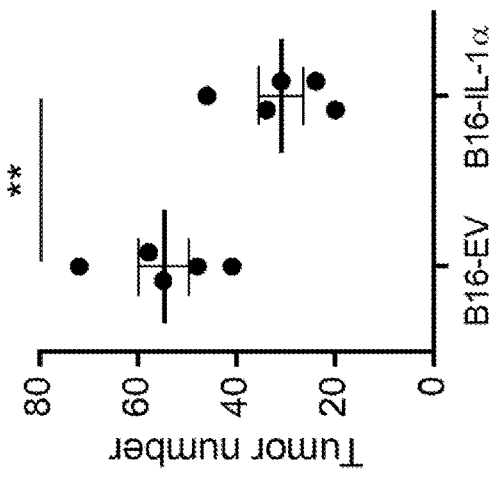
Figure 13E:
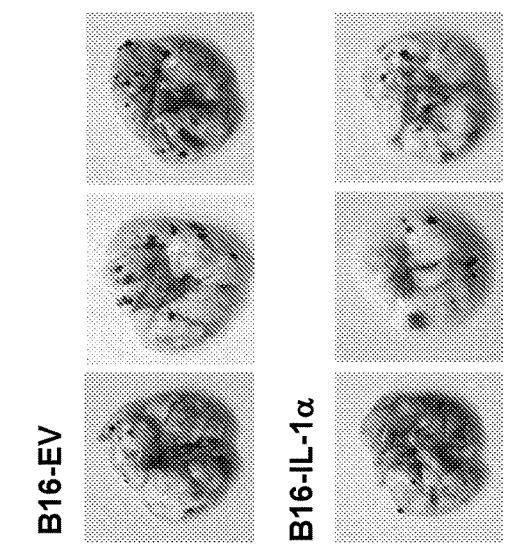
Figure 13D:
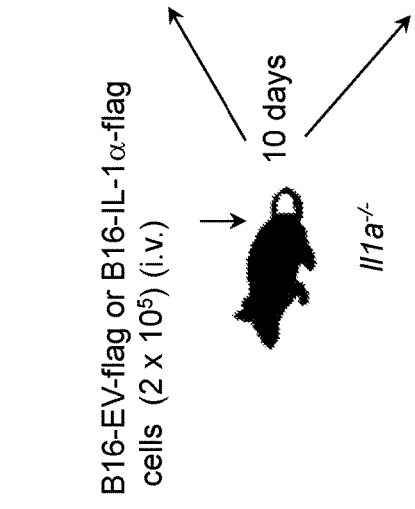

Intracellular IL-1α in B16 cells reduces melanoma metastasis. To investigate whether IL-1α has a direct role in melanoma metastasis, RFP stable expressing B16 cells were injected into WT or IL1α-/- mice, and then these B16-RFP positive cells were sorted by FACS from the metastatic lungs of those mice. 14 days later B16-RFP cells were isolated from lungs by flow sorting. B16-RFP sorted cells were then injected (i.v.) back into naive WT mice. B16 cells from WT mice had very inefficient melanoma colonization in the lungs after 14 days, whereas B16 cells isolated from Il1α-/- greater lung colonization (FIGS. 13A and 13B). Importantly, RFP expression did not affect B16 cell growth in vitro or the metastatic behavior in vivo. proIL-1α expression was found only in B16 cells from WT, but not in B16 cells from IL1α-/- mice (FIG. 9A). Interestingly, when we inject these cells are injected back into naive WT mice, B16 cells from WT mice (IL-1α expressing B16 cells) had very inefficient metastasis/melanoma colonization in the lungs, whereas B16 cells from IL1α-/- mice (IL-1α not expressing B16 cells) developed greater melanoma colonization in the lungs. (FIG. 9B). B16 cells isolated from IL1α-/- mice also had higher mitochondrial hexokinase-2 (HK-2) and Akt1 activation compared with B16 cells isolated from WT (FIG. 9C), which resulted in a higher glycolytic rate in B16 cells from Il1α-/- mice (FIG. 9D). Next, we generated IL-1α-flag or empty vector (EV)-flag stably cells (B16-IL-1α and B16-EV respectively) and injected them (i.v.) into Il1α-/- mice (FIG. 13D). B16-IL-1α cells had significantly less lung colonization compared to B16-EV cells (FIGS. 13E and 13F). Without being bound to any particular theory, these data suggest that host-derived IL-1α may be transferred into B16 cells during melanoma colonization in the lungs of WT mice, which in turn may lead to a reduction in Akt1 activation and glycolysis in B16 cells.

The iIL-1α-peptide reduces Akt1 activation and glycolysis in melanoma cells. The Akt1 serine/threonine kinase substrate consensus motif within the N-terminal pro-piece of IL-1α was identified (FIG. 10A), from which the short peptide derived from the human N-terminal IL-1α pro-piece was identified as a potential novel therapeutic agent. B16 or Yumm1.7 melanoma cells were treated with PBS or iIL-1α-peptide (40 μg/ml) for 5 hours, and HK-2 levels and Akt1 activation in the mitochondrial and cytosolic fraction were determined by western blot. It was found that the iIL-1α-peptide significantly reduced Akt1 phosphorylation (S473) and mitochondrial HK-2 in both B16 and YUMM1.7 cells (FIG. 10B). Consistent with these data, the glycolytic rate was decreased in iIL-1α-peptide treated B16 cells (FIG. 10C). Without being bound by any particular theory, the data indicates that the iIL-1α-peptide have an inhibitory effect on the PI3K/Akt1 pathway and glycolysis in melanoma cells.

Intracellular IL-1α reduced Akt1 activation. We found that B16 cells from Il1α−/− mice had higher Akt1 activation compared with B16 cells from WT mice (FIG. 14A). It was suggested that IL-1α selectively binds to acidic phospholipids such as phosphatidylserine and phosphatidylinositol, and we also observed proIL-1α interaction with phosphoinositides such as PI(4)P (PIP), PI(4,5)P2 (PIP2) and PI(3,4,5)P3 (PIP3) (FIG. 14B). Interestingly, PIP3 levels in the plasma membrane fraction of B16 cells from Il1α−/− (B16 cells not expressing IL-1α) was higher than that in B16 cells from WT (B16 cells expressing IL-1α) (FIG. 14C), suggesting that intracellular proIL-1α have an inhibitory effect on the PI3K/Akt1 pathway by interacting with PIP2.

Figure 12F:
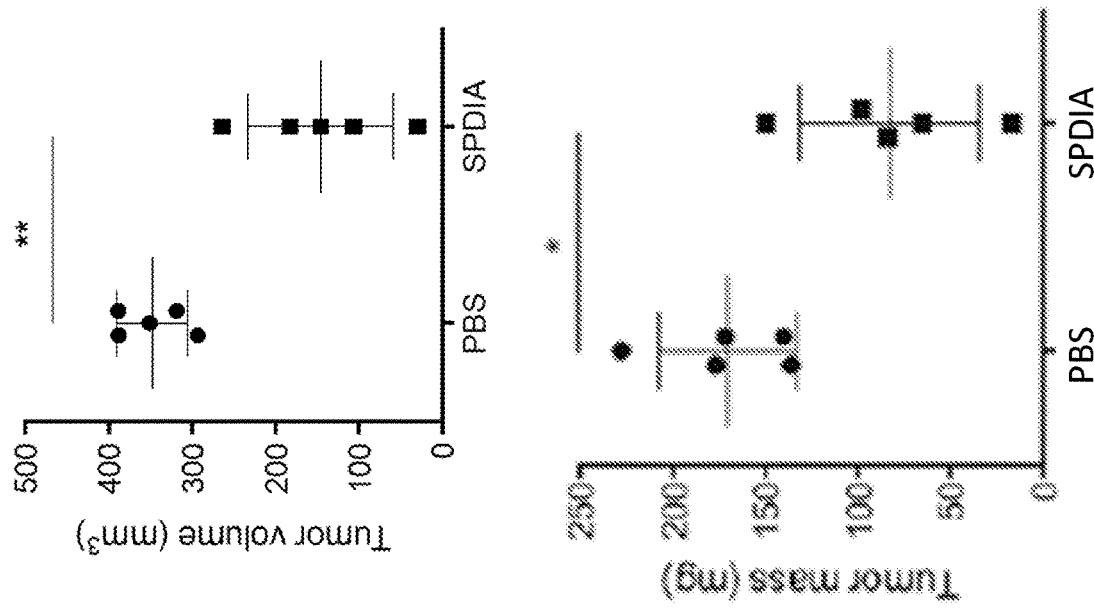
Figure 12D:
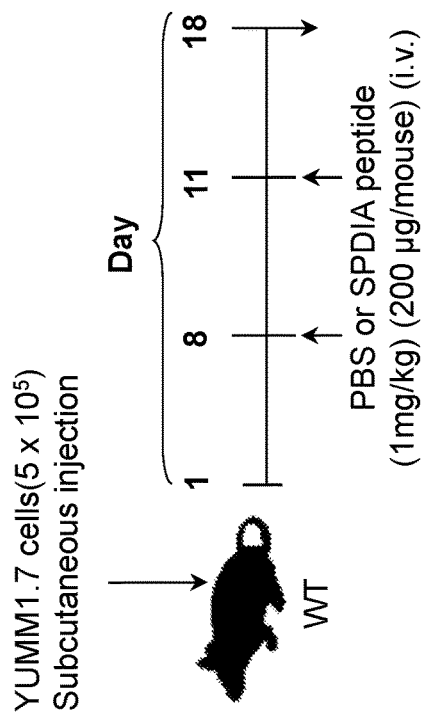
Figure 12E:
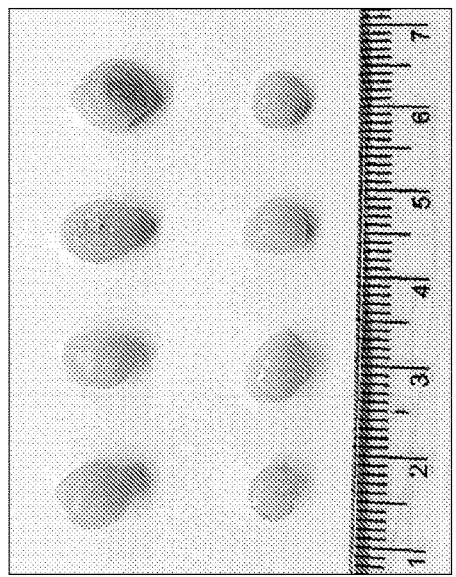

IL-1α pro-piece reduces melanoma tumor progression. To investigate the suppressive effect of intracellular proIL-1α in melanoma tumor progression, we designed a short Peptide Derived from IL-1A pro-piece (SPDIA) "GKVLKKRRLSL" (SEQ ID NO:1). SPDIA interacted with PIP and PIP2 similar to proIL-1α (FIG. 12A). However, if arginine residues (R) are replaced by alanine (A), the peptide fails to bind with PIP and PIP2 (FIG. 12B), and this was used as a control peptide (GKVLKKAALSL, SEQ ID NO:9). SPDIA significantly reduced Akt1 activation in both B16 and YUMM1.7 cells compared to control peptides (FIG. 12C), suggesting that SPDIA is sufficient to reduce Akt1 activation. Moreover, if we inject (i.v.) SPDIA peptide into WT mice with a YUMM1.7-cutaneous tumor, SPDIA peptide treatment reduced cutaneous melanoma tumor growth compared with PBS treated controls (FIG. 12D-F). These data indicate that SPDIA limit YUMM1.7 melanoma tumor growth.

The iIL-1α-peptide reduces tumor burden in vivo. The protective role of the iIL-1α-peptide against melanoma colonization was investigated. In the pilot study, B16 cells were injected into WT mice and these mice were treated with the iIL-1α-peptide on day 5 (i.v.) (FIG. 11A). The mice were analyzed 5 days later. It was observed that the iIL-1α-peptide treatment reduced melanoma colonization in the lungs compared with PBS treated controls (FIG. 11A-11C). Without being bound by any particular theory, this preliminary data indicates that the iIL-1α-peptide has therapeutic potential for protection against B16 melanoma colonization/metastasis.

The iIL-1α-peptide reduces genetically modified mouse melanoma cells (YUMM1.7)-induced cutaneous melanoma. WT mice were injected (subcutaneous) with $5\times10^5$ YUMM1.7 cells. The iIL-1α-peptide was injected (i.v.) (days 8 and 11) and mice were analyzed on day 18 (FIG. 12A). It was observed that the SPDIA peptide treatment reduced tumor volume and mass compared with PBS treated controls (FIGS. 12B and 12C). Without being bound by any particular theory, these data show that efficacy of the iIL-1α-peptide is not unique to the B16 mouse pulmonary melanoma model, as there was also a reduction in the volume and mass of human based genetically modified YUMM1.7 melanoma tumors.

The inventors sought to reveal the underlying cause of metastatic inefficiency of tumor cells, and the role of cell-to-cell communication between host and tumor cells in this process. The studies revealed that B16 cells developed increased melanoma tumor burden in IL1α−/− mice when compared with WT mice. It was found that host-derived pro-IL-1α transferred into B16 cells during melanoma colonization in the lungs, reduced tumor burden and metastatic potential of B16 cells by regulating Akt1 activation and glycolysis. Without being bound to any particular theory, this suggests that host IL-1α may be protective against melanoma tumor burden (FIG. 1). proIL-1α expression was found only in B16 cells isolated from WT mice, but not in B16 cells from IL1α−/− mice (FIG. 2A), which, without being bound by any particular theory suggests that there is an influence of the host on B16 cells. When these cells are injected back into naive WT mice, B16 cells from WT (IL-1α expressing B16 cells) had very inefficient metastasis/melanoma colonization in the lungs, whereas B16 cells from IL1α−/− (IL-1α not expressing B16 cells) developed aggressive melanoma colonization in the lungs (FIG. 2B). It was also found that Akt1 activation and glycolysis is reduced in IL-1α expressing B16 cells (FIGS. 2C and 2D). Additionally, the use of "YUMM1.7," a murine cell line harboring relevant human mutations, makes these results more translational. The short peptide derived from the human N-terminal iIL-1α-peptide (IL-1α pro-piece-SPDIA), when administered, significantly reduced Akt1 activation and glycolysis in melanoma cells. The identification of this peptide and its role in melanoma and metastasis, may lead to new avenues of investigation in drug discovery and potential novel therapeutics.

Transfer of IL-1α into Melanoma Cells, the Role of Intracellular IL-1α in Lung Metastasis Previous studies have shown that lung cells release functional mRNA and protein containing extracellular microvesicles (ExMVs), which can horizontally transfer into recipient cells. Importantly, stromal cells also constitutively express intracellular IL1α under normal physiological conditions. Without being bound by any particular theory, the inventors hypothesize that host IL-1α (mRNA or protein) is transferred into B16 cells by stromal cell-derived ExMVs, inhibiting the PI3K/Akt1 pathway and leading to reduced survival of melanoma cells and melanoma colonization in the lung.

YUMM1.7 cells are used to investigate the protective role of IL-1α against melanoma/metastasis and determine the host specific bioactive molecules in melanoma cells. RFP stable expressing YUMM1.7 melanoma cells are injected (i.v.) into WT or IL1α−/− mice, and after 5 and 14 days RFP positive cells are sorted from the lungs of those mice by fluorescence-activated cell sorting (FACS), and then total RNA and protein was isolated. Total RNA and protein from RFP expressing YUMM1.7 melanoma cell lines is isolated as a control. The RNA and protein screening are performed by RNA array and proteomics.

Total ExMVs are isolated from bronchoalveolar lavage fluid (BALF) of PBS or YUMM1.7 cells injected WT or IL1α−/− mice by exoEasy Maxi Kit (Qiagen), to determine if IL-1α is present in lung cell-derived ExMVs. Total RNA and protein is subsequently isolated by using a total exosome RNA and protein isolation kit, and IL-1α mRNA and protein is measured by qPCR and western blot (WB) respectively. A previous study found that lung specific genes transferred into bone marrow cells when co-cultured with the lung in vitro. Lungs from naïve WT or IL1α−/− are harvested and co-culture with YUMM1.7 melanoma cells in a transwell plate. The IL-1α mRNA and protein expression in YUMM1.7 cells are determined by qPCR and WB. Lung cell-specific RNA such as Clara cell specific-protein (CCSP) and surfactant protein B (SpB) are identified by PCR. ExMVs from culture medium is also isolated and IL-1α mRNA is measured in purified total ExMVs-derived RNA by PCR. IL-1α protein level in total ExMVs is also be determined by WB.

Mice are also injected with (subcutaneous) YUMM1.7-RFP cells into WT or IL1α−/− mice, to determine if IL-1α is present in circulating YUMM1.7 cells derived from a subcutaneous tumor. After the tumor size reaches 10 mm, circulating tumor cells (RFP positive) from blood of injected mice are analyzed by flow cytometry for IL-1α expression. YUMM1.7-RFP cells are also isolated from cutaneous tumor of those mice and IL-1α protein is determined by WB.

Without being bound to any particular theory, the inventors hypothesize that lung cell-specific mRNAs and proteins including IL-1α are present in malignant YUMM1.7 cells and that the IL-1α mRNA and protein in lung cells-derived ExMVs transfers into melanoma cells during melanoma colonization in the lung. In addition, similar to lung-isolated B16 cells, the inventors believe that cutaneous tumor-isolated YUMM1.7 cells are found with greater amounts of IL-1α in them when isolated from WT mice, compared with YUMM1.7 cells isolated from IL1α−/− mice.

The inventors further hypothesize that intracellular IL-1α may directly affect the PI3K/Akt1 pathway, leading to reduced survival and metastatic potential of melanoma cells and melanoma colonization in the lung. The role of intracellular IL-1α on metastatic inefficiency is determined. In previous data, B16 cells isolated from metastatic lungs of WT mice had very inefficient metastasis and melanoma colonization in the lungs. RFP stable expressing YUMM1.7 cells are isolated from metastatic lungs of WT or IL1α−/− mice, and injected back into naïve WT mice; tumor burden is analyzed in the lungs on day 14.

RFP expressing YUMM1.7 cells are isolated from metastatic lungs of WT or IL1α−/− mice to determine the role of immune cells on metastatic inefficiency. The isolated cells are injected back into naïve WT mice and immune cells from lungs of these mice are analyzed by flow cytometry at days 5 and 14. The immune cells are identified by the following surface markers: neutrophils: CD11b+ Ly6Ghi; NK cells: NK1.1+ CD3−; macrophages: CD11b+ F4/80+; DCs: CD11b+ CD11c+ MHCIIhi; CD4+ T cells: CD3+ CD4+; CD8+ T cells: CD3+ CD8+ and B cells: CD19+. In addition, surface markers on tumor cells such as MHC I are determined.

RFP expressing YUMM1.7 cells are injected (i.v.) into WT and IL1α−/− mice to determine the extravasation of melanoma cells in the lung. After 3 and 5 days, lungs are harvested and extravasated melanoma cells are analyzed by flow cytometry. Lungs are also embedded in paraffin and RFP positive cells in paraffin sections are analyzed by fluorescence microscopy.

ProIL-1α-flag cDNA is transfected into YUMM1.7 cells to determine the crosstalk between intracellular IL-1α and PI3K/Akt1 pathway. IL-1α-Akt1 interaction is determined using the stable cell line generated. IL-1α is immunoprecipitated by anti-flag antibody, and then IL-1α and Akt1 are detected by WB. In the same samples, IL-1α phosphorylation is determined by WB using anti-Akt1 substrate and anti-phosphoserine antibodies. The activation of PI3K/Akt1 pathway signaling molecules such as PDK, mTORC2, PI3K (p85 and p110), PIP2, PIP3 and Akt1 in cell lysates of proIL-1α-flag expressing YUMM1.7 cells are evaluated by WB. Empty-vector transfected cells are used in all control experiments. In addition, mutant Akt1 consensus motif within proIL-1α-flag cDNA are generated to create a mutant proIL-1α stable expressing YUMM1.7 cell line used in immunoprecipitation experiments for proIL-1α-Akt1 interaction.

Similar to B16 cells, without being bound to any particular theory, the inventors hypothesize that YUMM1.7 cells obtained from WT mice have inefficient metastasis and reduced melanoma colonization in the lung. IL-1α expressing YUMM1.7 cells are not believed to alter immune cell infiltration into the lungs of WT mice and host IL-1α will transfer into YUMM1.7 cells during melanoma colonization, but not early extravasation (at days 3 and 5) into the lungs of WT mice. In preliminary studies, Akt1 activation is reduced in proIL-1α expressing B16 cells (FIG. 2C), and Akt1 consensus substrate motif containing the short peptide reduced Akt1 activation in melanoma cells (FIG. 3). Without being bound to any particular theory, the inventors believe that there will be direct interaction between proIL-1α and pAkt1, and the Akt1 consensus motif of IL-1α plays role in that interaction.

Mechanism by which the iIL-1α-Peptide Regulates PI3K/Akt1 Pathway in Melanoma Cells and Characterization of the Role of the Novel Therapeutic Agent in Preventing Lung Metastasis Previous studies have shown that intracellular IL-1α (proIL-1α) is released from necrotic cells and triggers IL-1α extracellular signaling cascade as well as its secreted form, which is known to be tumorigenic, and necrosis generally occurs within tumors. However, IL-1α pro-piece induces apoptosis in malignant tumor cells in vitro, which does not contain the IL-1α receptor signaling sequence. Preliminary data identified an Akt1 substrate consensus motif within the IL-1α pro-piece (iIL-1α-peptide), from which a short peptide derived from the human N-terminal IL-1α propiece (IAPP) was designed as a novel therapeutic agent, which contained the Akt1 substrate consensus motif. Administration of this peptide significantly reduced Akt1 activation and glycolysis in B16 cells (FIG. 3). The inventors hypothesize that iIL-1α-peptide may act as a pseudosubstrate inhibitor for the PI3K/Akt1 pathway in melanoma cells, which reduces the survival and metastatic potential of the tumor cells and prevents lung metastasis.

The IL-1α nuclear localization sequence is responsible for proIL-1α nuclear localization, and it can penetrate cell membranes without any carrier. The iIL-1α-peptide contains both the Akt1 substrate consensus motif and the nuclear localization sequence of human IL-1α and is used to determine the crosstalk by which the iIL-1α-peptide regulates the PI3K/Akt1 pathway in melanoma cells.

The iIL-1α-peptide was labeled with VivoTag 680XL Protein Labeling Kit (PerkinElmer) to determine its cell membrane penetrating efficiency and cellular toxicity of the iIL-1α-peptide. B16 and YUMM1.7 melanoma cells are treated with 680-labeled IAPP peptide (at various doses and durations), and intracellular expression of the iIL-1α-peptide is detected by fluorescence microscopy. The nuclear localization sequence of the iIL-1α-peptide is also mutated and used as a negative control. Further, the cellular cytotoxicity of the melanoma cells and the half-life of the iIL-1α-peptide is measured using the LDH cytotoxicity assay kit and fluorescence microscopy.

Preliminary data demonstrated that the iIL-1α-peptide reduced Akt1 activation and glycolysis in melanoma cells. B16 or YUMM1.7 cells are treated with PBS or the iIL-1α-peptide (at various doses and time points) to determine the inhibitory effect of the iIL-1α-peptide on the PI3K/Akt1 pathway. Phosphorylation of PI3K (p85 and p110), PIP2, PIP3, PDK1 and mTORC2 in cell lysates are determined by western blot. Glycolysis and respiration (as a control) are measured using Seahorse as before. Peritoneal macrophages are also treated with the iIL-1α-peptide to determine if the iIL-1α-peptide alters non-cancer cells glycolysis. Without being bound to any particular theory, the inventors believe that the iIL-1α-peptide successively penetrates into the melanoma cells and directly regulates PI3K/Akt1 pathway.

To investigate and characterize the therapeutic effect of the iIL-1α-peptide in lung metastasis and determine the dose and delivery target of the iIL-1α-peptide in vivo, YUMM1.7 cells are injected (i.v.) into WT mice, and starting at day 5 PBS or different doses of iIL-1α-peptide are injected into the tail vein every 2 days. Tumor burden in the lungs is analyzed at day 14. Separately, the iIL-1α-peptide is labeled with the VivoTag 680XL Protein Labeling Kit (PerkinElmer) to determine in vivo distribution and half-life of the iIL-1α-peptide. WT mice are injected with RFP-YUMM1.7 cells via tail vein or cutaneously, and on day 14 are injected (i.v.) with labeled 680XL-iIL-1α-peptide, and in vivo imaging is performed at days 15 and 16 by using the IVIS® Lumina XR Optical Imaging System at Cedars-Sinai, Imaging Core Lab.

To determine the role of iIL-1α-peptide on anti-tumor immunity in vivo, YUMM1.7 cells are injected (i.v.) into WT mice, and at days 5 and 7 are injected (i.v.) with PBS or iIL-1α-peptide. At day 10 the immune cells from lungs and blood are analyzed by flow cytometry and the immune cells are identified as discussed above.

RFP-YUMM1.7 cells isolated from lungs of WT mice are injected (i.v.) into WT mice to determine the therapeutic effect of the iIL-1α-peptide in lung metastasis. PBS or iIL-1α-peptide are injected (at day 1, 3 and 5) by tail vein and tumor burden in the lungs is analyzed at day 14. Circulating tumor cells (RFP positive cells) from blood of these mice is also analyzed by flow cytometry for apoptosis (annexin V staining) to investigate if the iIL-1α-peptide treatment is inducing apoptosis in the tumor cells in vivo.

Without being bound to any particular theory, the inventors believe that the iIL-1α-peptide will reduce metastatic potential of melanoma cells by regulating the PI3K/Akt1 pathway and prevent lung metastasis. The PI3K/Akt1 is known to play an important role in tumor cell survival. Additionally, glycolysis is known to benefit cancer cell growth. Thus, it is likely that the iIL-1α-peptide is negatively affecting the tumor cells ability to colonize the lungs by altering its survivability in vivo. Finally, as the iIL-1α-peptide does not contain the IL-1α signaling sequence, when delivered into host stromal and immune cells, the iIL-1α-peptide should not induce an inflammatory signal.

Example 3

To investigate metastatic efficiency, we also exploit the Braf$^{CA}$Pten$^{loxP}$Tyr:CreER$^{T2}$ autochthonous murine model of melanoma (hereafter referred to as the Braf/Pten model). Briefly, following hair removal from the dorsal flank of 6-week-old male and female Braf/Pten mice (currently in our vivarium), 20 μl of 20 mM 4-hydroxytamoxifen (4-HT) are applied topically and allowed to dry. At 0, 2, 4, and 6 weeks after mice develop palpable tumors they will be euthanized and primary and metastatic tumors characterized. Unlike the B16 mouse model, the Braf/Pten model undergoes tumorigenesis with development first of local melanoma with subsequent progression to true metastatic disease.

Example 4

IL-1α is constitutively expressed in stromal cells under normal physiological conditions and without wishing to be bound by any particular theory, the inventors believe that host IL-1α transfers into melanoma cells by stromal cell-derived ExMVs.

We inject (i.v.) RFP stable expressing YUMM1.7 melanoma cells into WT or Il1a−/− mice; after 14 days YUMM1.7 cells (RFP+) are sorted from the lungs of those mice via flow cytometry. Total RNA is isolated and sequenced (RNA-seq) by NextSeq 500 platform (Illumina) using 75 bp single-end sequencing, data analysis is performed by STAR (version 2.5.0) (Cedars-Sinai Genomics Core). The precise protein fingerprint of the tumor cells is also determined (Mass Spectrometry and Biomarker Discovery Core). Samples are prepared using the Beckman NXp automated workstation. Tryptic peptides are analyzed by liquid chromatography-tandem mass spectrometry (LC-MS), using an LTQ Orbitrap Elite mass spectrometer connected to an EASY-nLC1000 liquid chromatography system. Proteins are identified and quantified using MaxQuant proteomics software. We also isolate total RNA and protein from RFP expressing YUMM1.7 cells grown in vitro as a control. (5 mice/group×2 genotypes×3 replicates=30 mice)

Total ExMVs are isolated from bronchoalveolar lavage fluid (BALF) of WT or Il1a−/− mice injected (i.v.) with YUMM1.7 cells using an exoEasy Maxi Kit (Qiagen). Total exosome RNA and protein are isolated and IL-1α mRNA and protein are measured by quantitative RT-PCR (qPCR) and western blot (WB), respectively. ExMVs are isolated from naïve WT mice and transferred (intratracheally) into RFP-YUMM1.7 cells injected (i.v.) Il1a−/− mice at day 5 and 10. YUMM1.7 cells are then isolated at day 14 by flow cytometry and IL-1α mRNA and protein expression is determined by qPCR and WB. A previous study found that lung specific RNA transferred into bone marrow cells when co-cultured with the lung suspension in vitro. Utilizing this technique, single cell lung suspension from naïve WT or Il1a−/− mice is co-cultured with YUMM1.7 melanoma cells in a transwell plate. The IL-1α mRNA and protein expression in YUMM1.7 cells are determined by qPCR and WB. Lung cell-specific RNA such as Clara cell specific-protein (CCSP) and surfactant protein B (Sp-B) are identified by qPCR. (5 mice/group×2 conditions×2 genotypes×3 replicates=60 mice)

While not wishing to be bound by any particular theory, the inventors believe that there will be lung cell-specific mRNAs and proteins, including IL-1α, in malignant YUMM1.7 cells isolated from lungs. We also believe that IL-1α mRNA and protein will be in host derived ExMVs, which will transfer into melanoma cells during lung colonization.

Example 5

Our data show that intracellular proIL-1α reduces melanoma survival and may be linked to defective PIK3/Akt1 signaling. Therefore, while not wishing to be bound by any particular theory, we believe that intracellular proIL-1α may have an inhibitory effect on the PI3K/Akt1 pathway leading to the metastatic inefficiency of melanoma cells.

To determine if host IL-1α reduces tumor growth and transition to metastatic disease, we cross mice with Braf/Pten mice (both in our vivarium; described above) to generate melanoma-susceptible mice lacking IL-1α. Braf/Pten/Il1a+/+ and Braf/Pten/Il1a−/− mice are treated with topical tamoxifen and assessed for: 1) time to tumor development; and 2) tumor size and progression. Primary tumors and metastatic lesions (lymph node and lung) are dissected and evaluated histologically. Tumors are scored in a blinded fashion by a pathologist to determine radial (in situ or microinvasive) or vertical growth phases. Melanoma in vertical growth phase will be further scored for number of mitoses and culature structures. (5 mice/group×2 genotypes×3 replicates=30 mice)

Example 6

To determine if IL-1α deficiency affects tumor associated-immune cells, Braf/Pten/Il1α+/+ and Braf/Pten/Il1α−/− mice are treated with topical tamoxifen and at 6 weeks after tumor induction, tumors, lymph nodes, lungs and liver are dissected, and cell populations analyzed by flow cytometry. We identify tumor-associated macrophages (TAM) as CD45+CD11b+F4/80hi, polymorphonuclear-myeloid-derived suppressor cells as CD11b+Ly6CloLy6G+, CD8 T cells as CD45+CD3+CD8+, CD4 T cells as CD45+CD3+CD4+, regulatory T cells (Tregs) as CD45+CD3+CD4+CD25+. (5 mice/group×2 genotypes×3 replicates=30 mice)

Example 7

We generate proIL-1α-flag stably expressing YUMM1.7 cells to determine the interaction between proIL-1α and phosphatidylinositol 4,5-biphosphate (PIP2). PIP2 is immunoprecipitated from the cell lysates and then proIL-1α is detected by WB using anti-flag or anti-IL-1α antibody. If we find proIL-1α-PIP2 interaction, we will mutate amino acids within the N-terminal pro-piece of IL-1α (GKVLKKRRLSL) (SEQ ID NO:1) and generate mutant proIL-1α-flag stably expressing YUMM1.7 cell lines, and determine the proIL-1α binding site for PIP2 followed by immunoprecipitation experiments as described above. We also evaluate immunocytochemical colocalization between proIL-1α and PIP2 in proIL-1α-flag stably expressing YUMM1.7 cells (Leica TCS SP confocal microscopy).

While not wishing to be bound by any particular theory, the inventors believe that Braf/Pten/Il1α−/− mice are expected to develop larger tumors and metastatic disease and may have more tumors with evidence of vertical rather than radial growth compared with Braf/Pten/Il1α+/+ mice. In our data, Akt1 activation and PIP3 levels were reduced in proIL-1α-expressing B16 cells (B16 from WT) and recombinant proIL-1α directly interacted with PIP and PIP2, thus we expect that there will be direct interaction between proIL-1α and PIP2, and reduced PIP3 and Akt1 activation in YUMM1.7 melanoma cells. We also expect that melanoma cells (CD45−CD146+) from primary tumors of Braf/Pten/Il1α−/− mice will have higher Akt1 activation compared to melanoma cells from Braf/Pten/Il1α+/+ mice.

Example 8

While not wishing to be bound by any particular theory, the inventors believe that the SPDIA peptide directly interact with PIP2, interfering with PIP ced Akt1 activation in melanoma cells. This ultimately has an inhibitory effect on melanoma tumor growth and transition to metastatic disease.

As our SPDIA peptide contains the nuclear localization sequence of IL-1α and we believe that the SPDIA peptide is able to penetrate the melanoma cell membrane.

We label the SPDIA peptide with 680XL tag (680XL-SPDIA) using the VivoTag 680XL Protein Labeling Kit (PerkinElmer) for determine half-life and membrane penetrating efficiency of SPDIA peptide. B16 or YUMM1.7 melanoma cells are treated with 680XL-SPDIA peptide at various doses (10-100 μg/ml) and durations (1-10 h), and live images for intracellular expression and half-life of the SPDIA peptide are detected by fluorescence microscopy (Keyence, BZ-X). Further, the cellular cytotoxicity to the B16 and YUMM1.7 melanoma cells are measured by LDH cytotoxicity assay kit.

We conjugate a Flag tag to SPDIA or a Control peptide (by GenScript); SPDIA-flag or Control-flag. We treat YUMM1.7 cells with SPDIA-flag or Control-flag peptides and determine the interaction between SPDIA peptide and phosphatidylinositol 4,5-biphosphate (PIP2); PIP2 is immunoprecipitated from the cell lysates and then flag-tag (for SPDIA and Control peptide) are detected by Anti-Flag High Sensitivity ELISA kit (Sigma). We also determine levels of PIP3 and Akt1 responsible kinases (PDK1 and mTORC2) in membrane and cytosolic fractions by WB. In a separate experiment, we will treat YUMM1.7 cells with 680XL-SPDIA or 680XL-Control peptides, and after fixation the cells are stained with anti-PIP2-Alexa-488 antibody and co-localization between SPDIA peptide and PIP2 will be measured by confocal microscopy (Leica, TCS SP).

While not wishing to be bound by any particular theory, the inventors believe that that the SPDIA peptide will successfully penetrate into the melanoma cells and reduce PIP3 generation and Akt1 activation. In our data, melanoma cells were treated with 40 μg/ml of SPDIA peptide for 5 h, which significantly reduced Akt1 activation, without inducing cytotoxicity under those conditions. While we do next expect to observe any cytotoxicity in vitro, at cells at lower concentrations of SPDIA peptide for longer durations (24, 48 h) and assess cell death.

Example 9

While not wishing to be bound by any particular theory, the inventors believe that SPDIA peptide reduces the survival and the metastatic potential of the melanoma cells resulting in diminished tumor growth and transition to metastatic diseases in the Braf/Pten genetically modified mouse model.

To determine half-life and delivery site of SPDIA peptide, we inject (i.v.) 680XL-SPDIA peptide at various doses (1-5 mg/kg) into Braf/Pten mice 6 weeks after tumor induction and then perform daily in vivo imaging (to determine half-life) using the IVIS Lumina XR Optical Imaging System at the Cedars-Sinai Imaging Core Lab. (5 mice/group×5 conditions×3 replicates=75 mice)

To determine if the SPDIA peptide reduces tumor growth and transition to metastatic disease, we inject (i.v.) Control or SPDIA peptide (1-5 mg/kg) at every 2 days into Braf/Pten mice after development of palpable tumors and assess tumor size and progression. Six weeks post-tumor induction, histology of primary tumors and metastatic lesions are evaluated. Tumors are scored in a blinded fashion by a pathologist to determine radial (in situ or microinvasive) or vertical growth phases. Melanoma in vertical growth phase is further scored for number of mitoses and presence or absence of invasion of vasculature structures. Tumors, lymph nodes, lungs and liver are dissected and melanoma cells (CD45−CD146+) will be sorted by flow cytometry to determine Akt1 activation by WB. (5 mice/group×2 conditions×3 replicates=30 mice)

To determine if the SPDIA peptide alters tumor associated-immune cell populations, Braf/Pten mice are treated with topical tamoxifen, and after development of palpable tumors, mice will receive SPDIA or Control peptide. Tumors, lymph nodes, lungs, and liver are dissected and cell populations will be analyzed by flow cytometry; tumor-associated macrophages (TAM) as CD45+CD11b+F4/80hi, monocytic-myeloid-derived suppressor cells (M-MDSCs) as CD11b+Ly6ChiLy6G- and polymorphonuclear-myeloid-derived suppressor cells as CD1 lb+Ly6CloLy6G+, CD8 T cells as CD45+CD3+CD8+, CD4 T cells as CD45+CD3+CD4+, regulatory T cells as CD45+CD3+CD4+CD25+.

Based on our data, and while not wishing to be bound by any particular theory, the inventors believe that the SPDIA peptide reduce the survival of melanoma cells by regulating the PI3K/Akt1 pathway and reduce tumor development and metastasis. PI3K/Akt1 is known to play an important role in tumor cell survival. Similar to B16F10 and YUMM1.7 cells, we believe that the SPDIA peptide will reduce Akt1 activation in melanoma cells (CD45-CD146+) from primary tumors in Braf/Pten mice compared with Control peptide. Thus, the SPDIA peptide inhibits tumor cell growth and metastatic potential. As our SPDIA peptide does not contain the IL-1α receptor signaling sequence, we expect that the SPDIA peptide will not activate immune cells.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for reducing and/or reducing the likelihood of cancer metastasis in a subject in need thereof, comprising:
    administering a therapeutically effective dosage of a pro-interleukin-1α (pro-IL-1α) peptide mimic to the subject to reduce and/or reduce the likelihood of the cancer metastasis,
    wherein the pro-IL-1α peptide mimic consists of the amino acid sequence of SEQ ID NO: 1, or
    wherein the pro-IL-1α peptide mimic consists of the amino acid sequence of SEQ ID NO: 1 with 1, 2, or 3 amino acid substitutions, deletions or additions.

2. The method of claim 1, wherein the pro-IL-1α peptide mimic consists of the amino acid sequence of SEQ ID NO: 1.

3. The method of claim 1, wherein the pro-IL-1α peptide mimic is formulated in a composition.

4. The method of claim 1, wherein the metastasis of lung cancer and/or melanoma is reduced.

5. The method of claim 1, wherein administering the therapeutically effective dosage of the pro-IL-1a peptide mimic reduces AKT serine/threonine kinase 1 (AKT1) activation and glycolysis in the cancer cells.

6. The method of claim 1, wherein AKT1 phosphorylation in the cancer cells is reduced.

7. The method of claim 1, wherein the glycolic rate in the cancer cells is decreased.

* * * * *